United States Patent
Ayata et al.

(10) Patent No.: US 12,296,167 B2
(45) Date of Patent: May 13, 2025

(54) SYSTEMS AND METHODS FOR CONTROLLING AGAINST ANEURYSM FORMATION, GROWTH AND RUPTURE, AND IMPROVING POST-RUPTURE OUTCOMES

(71) Applicant: THE GENERAL HOSPITAL CORPORATION, Boston, MA (US)

(72) Inventors: Cenk Ayata, Sudbury, MA (US); Aman B. Patel, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 831 days.

(21) Appl. No.: 17/295,099

(22) PCT Filed: Nov. 20, 2019

(86) PCT No.: PCT/US2019/062403
§ 371 (c)(1),
(2) Date: May 19, 2021

(87) PCT Pub. No.: WO2020/106833
PCT Pub. Date: May 28, 2020

(65) Prior Publication Data
US 2022/0016424 A1 Jan. 20, 2022

Related U.S. Application Data

(60) Provisional application No. 62/769,847, filed on Nov. 20, 2018.

(51) Int. Cl.
*A61N 1/36* (2006.01)
*A61N 1/04* (2006.01)

(52) U.S. Cl.
CPC ........ *A61N 1/36034* (2017.08); *A61N 1/0456* (2013.01)

(58) Field of Classification Search
CPC .............. A61N 1/36034; A61N 1/0456; A61N 1/36053; A61N 1/36014; A61B 5/02014
See application file for complete search history.

(56) References Cited

U.S. PATENT DOCUMENTS

| 5,611,350 A | * | 3/1997 | John | ................... | A61N 1/3605 |
| | | | | | 607/45 |
| 8,788,044 B2 | * | 7/2014 | John | .................. | A61N 1/36064 |
| | | | | | 607/46 |

(Continued)

FOREIGN PATENT DOCUMENTS

WO 2020106833 A1 5/2020

OTHER PUBLICATIONS

Ay et al., "Electrical Stimulation of the Vagus Nerve Dermatome in the External Ear is Protective in Rat Cerebral Ischemia," Brain Stimulation 8 (2015) 7-12.

(Continued)

*Primary Examiner* — Carl H Layno
*Assistant Examiner* — Aya Ziad Bakkar
(74) *Attorney, Agent, or Firm* — QUARLES & BRADY LLP

(57) ABSTRACT

A system and method is provided for improving the patient outcome for a subject having an aneurysm. The method includes determining that the subject has the aneurysm, positioning a vagus nerve stimulation system on the subject, the vagus nerve stimulation system being configured to provide an electrical stimulation to the vagus nerve of the subject. Stimulating the vagus nerve of the subject with the vagus nerve stimulation system to at least one of: prevent further growth of the aneurysm; decrease the likelihood that the aneurysm ruptures; and decrease effects of rupture, when the aneurysm of the subject ruptures.

14 Claims, 15 Drawing Sheets

(56) References Cited

U.S. PATENT DOCUMENTS

| | | | |
|---|---|---|---|
| 2008/0249439 A1 | 10/2008 | Tracey et al. | |
| 2009/0125076 A1* | 5/2009 | Shuros | A61N 1/36114 607/17 |
| 2009/0292324 A1 | 11/2009 | Rousso et al. | |
| 2010/0069995 A1 | 3/2010 | Danielsson | |
| 2010/0312096 A1* | 12/2010 | Guttman | A61B 5/415 600/411 |
| 2011/0137405 A1 | 6/2011 | Wilson et al. | |
| 2013/0253413 A1 | 9/2013 | Levine et al. | |
| 2013/0317580 A1* | 11/2013 | Simon | A61N 2/006 607/115 |

OTHER PUBLICATIONS

Ay et al., "Transcutaneous Cervical Vagus Nerve Stimulation Ameliorates Acute Ischemic Injury in Rats," Brain Stimulation 9 (2016) 166-173.

Ay et al., "Vagus nerve stimulation reduces infarct size in rat focal cerebral ischemia: An unlikely role for cerebral blood flow," Brain Research 1392 (2011) 110-115.

Aydin et al., "The role of ischemic neurodegeneration of the nodose ganglia on cardiac arrest after subarachnoid hemorrhage: An experimental study," Experimental Neurology 230 (2011) 90-95.

Chalouhi et al., Biology of intracranial aneurysms: role of inflammation, Journal of Cerebral Blood Flow & Metabolism (2012) 32, 1659-1676.

Chen et al., "Vagus nerve stimulation inhibits cortical spreading depression," Pain, vol. 157 (2016) 797-805.

Chu et al., "Myeloperoxidase Is Increased in Human Cerebral Aneurysms and Increases Formation and Rupture of Cerebral Aneurysms in Mice," Stroke, (2015) 46:1651-1656.

Hosaka et al., "Inflammation and Cerebral Aneurysms," Transl. Stroke Res. (2014) 5:190-198.

International Search Report and Written Opinion issued in corresponding PCT Application No. PCT/US2019/062403, issued Jan. 28, 2020.

Johnson et al., "A review of vagus nerve stimulation as a therapeutic intervention," Journal of Inflammation Research (2018); 11:203-213.

Kanematsu et al., "Critical Roles of Macrophages in the Formation of Intracranial Aneurysm," Stroke, (2011) 42:173-178.

Kataoka et al., Structural Fragility and Inflammatory Response of Ruptured Cerebral Aneurysms: A Comparative Study Between Ruptured and Unruptured Cerebral Aneurysms, Stoke, Jul. 1999.

Lu et al., "Nicotinic Acetylcholine Receptor Alpha7 Subunit Mediates Vagus Nerve Stimulation-Induced Nuroprotection in Acute Permanent Cerebral Ischemia by a7nAchR/JAK2 Pathway," Med Sci Monit, 2017; 23:6072-6081.

Makino et al., "Pharmacological Stabilization of Intracranial Aneurysms in Mice," Stroke, (2012) 43:2450-2456.

Mourdoukoutas et al., "High-Resolution Multi-Scale Computational Model for Non-Invasive Cervical Vagus Nerve Stimulation," Nuromodulation: Technology at the Nural Interface, (2018); 21: 261-268.

Nonis et al., "Evidence of activation of vagal afferents by non-invasive vagus nerve stimulation: An electrophysiological study in healthy volunteers," Cephalalgia (2017) vol. 37(13) 1285-1293.

Nowicki et al., "M1 macrophages are required for murine cerebral aneurysm formation," Basic Science, J NeuroIntervent Surge 2018; 10:93-97. doi:10.1136/neurintsurg-2016-012911.

Nuki et al., "Elastase-Induced Intracranial Aneurysms in Hypertensive Mice," Hypertension, Dec. 2009.

Ota et al., "Roles of matrix metalloproteinases in flow-induced outward vascular remodeling," Journal of Cerebral Blood Flow & Metabolism (2009) 29, 1547-1558.

Petrofsky et al., "The transfer of current through skin and muscle during electrical stimulation with sine, square, Russian and interferential waveforms," Journal of Medical Engineering & Technology, vol. 33, No. 2, Feb. 2009, 170-181.

Powell et al., "The Potential Role of Neuromodulation in Subarachnoid Hemorrhage," Neuromodulation (2021) 1-12.

Ryba et al., "Influence of Vagal Input on Cerebral Blood Flow in Monkeys and Dogs After Eperimental Cerebral Vasospasm," Acta Neurobiol, Exp. 1985, 45: 163-171.

Shimada et al., "Protective Role of Peroxisome Proliferator-Activated Receptor-y in the Development of Intracranial Aneurysm Rupture," Stroke, (2015) 46:1664-1672. doi: 10.1161/strokeaha.114. 007722.

Starke et al., "Critical role of TNF-a in cerebral aneurysm formation and pregression to rupture," Journal of Neuroinflammation (2014) 11:77.

Suzuki et al., "Noninvasive Vagus Nerve Stimulation Prevents Ruptures and Improves Outcomes in a Model of Intracranial Aneurysm in Mice," Stroke, May 2019, pp. 1216-1223.

Wang et al., "Nicotinic acetylcholine receptor a7 subunit is an essential regulator of inflammation," Nature, vol. 421, Jan. 2003.

Wang et al., "Low-level Transcutaneous Electrical Stimulation of the Auricular Branch of Vagus Nerve Ameliorates Left Ventricular Remodeling and Dysfunction by Downregulation of Matrix Metalloproteinase 9 and Transforming Growth Factor B1," J Cardiovasc Pharmacol, (2015) 65:342-348.

Watanabe et al., "Suppression of abdominal aortic aneurysm formation by AR-R17779, an agonist for the a7 nicotinic acetylcholine receptor," Atherosclerosis 244 (2016) 113-120.

Yang et al., "Non-invasive vagus nerve stimulation reduces blood-brain barrier disruption in a rat model of ischemic stroke," Brain Stimulation 11 (2018) 689-698.

* cited by examiner

SYSTEMS AND METHODS FOR CONTROLLING AGAINST ANEURYSM FORMATION, GROWTH AND RUPTURE, AND IMPROVING POST-RUPTURE OUTCOMES

CROSS-REFERENCE TO RELATED APPLICATIONS

This application is a U.S. National Stage of International Application No. PCT/US2019/062403 filed Nov. 20, 2019 which is based on, claims the benefit of, and claims priority to U.S. Provisional Application No. 62/769,847, filed Nov. 20, 2018, which is hereby incorporated by reference herein in its entirety for all purposes.

STATEMENT REGARDING FEDERALLY SPONSORED RESEARCH

This invention was made with government support under P01NS055104 and R01NS102969, awarded by the National Institutes of Health. The government has certain rights in the invention.

BACKGROUND

A subarachnoid hemorrhage ("SAH") is a life threatening condition, which is defined by bleeding into the subarachnoid space (i.e., the region defined between the arachnoid membrane and the pia matter). SAH can be caused by many different, and seemingly unrelated conditions. For example, SAH can be caused by a head injury, a ruptured cerebral aneurysm, vascular malformations (such as brain arteriovenous malformations), drug usage, and other causes. Of the diverse causes for SAH, aneurysms, with their myriad causes, is particularly prominent, complex, troubling and most devastating. An aneurysm is a localized enlargement of a vessel caused by a weakening of the vessel wall in that localized area.

Regardless of the underlying causes, typically, once bleeding into the subarachnoid space commences, intervention must be conducted swiftly in order to prevent lasting damage to the brain tissue and prevention of a second rupture. SAH can cause blood to pool (and sometimes clot) within the subarachnoid space. This increases the mass of fluid constrained within the skull, which thereby increases the intracranial pressure, crushing delicate brain tissue, or in some cases, causing the brain to shift and herniate. SAH can also obstruct normal cerebrospinal fluid flow, causing swelling of the ventricles (hydrocephalus). Lastly, blood within the subarachnoid space can cause nearby arteries within the brain to spasm and contract (e.g., vasospasm). The contraction of the nearby arteries is especially dangerous, at least because it can obstruct normal blood flow, depriving downstream blood vessels of oxygenated blood, which can cause irreversible damage to those tissues.

The complications associated with SAH occur quickly, and in some cases, one complication can exacerbate another complication. For example, areas of the brain downstream from the bleeding site deprived of oxygenated blood, can have more severe injury due to the increases in intracranial pressure (e.g., by further occlusion of those vessels). Thus, not surprisingly, SAH is considered an extremely time-sensitive condition, necessitating immediate intervention. As such, once SAH has been confirmed, interventional drugs and procedures are administered and conducted almost immediately. Examples of a surgical interventions are endovascular coiling and surgical clipping, which are procedures to eliminate blood flow into the aneurysm space by filling the aneurysm with soft platinum coils (coiling) or placement of a clip across the base of the aneurysm (clipping). Although surgical intervention can help increase patient outcomes, it is not foolproof. Often, complications associated with SAH persist even when surgical procedures have fixed the problem (e.g., prevent additional blood from leaking into the aneurysm space). For example, if brain tissues have been starved of oxygenated blood for long periods of time, in some cases, no drugs or other interventions can reverse the damage.

Thus, it would be desirable to have improved systems and methods for controlling or preventing conditions leading to aneurysms and SAH, and to improve post-rupture outcomes by reducing risks of associated complications related to SAH.

SUMMARY OF THE DISCLOSURE

Systems and methods are provided for improving the patient outcome for a subject at risk of or experiencing an SAH. The method can include determining that the subject has the aneurysm, positioning a vagus nerve stimulation system on the subject, the vagus nerve stimulation system can be configured to provide an electrical stimulation to the vagus nerve of the subject. Stimulating the vagus nerve of the subject with the vagus nerve stimulation system to at least one of: prevent further growth of the aneurysm; decrease a likelihood that the aneurysm ruptures; and decrease effects of rupture, when the aneurysm of the subject ruptures.

Some non-limiting examples of the disclosure provide a method for improving the patient outcome for a subject having an intracranial hemorrhage. The method can include determining that the subject has the intracranial hemorrhage, and positioning a vagus nerve stimulation system on the subject. The vagus nerve stimulation system can be configured to provide an electrical stimulation to the vagus nerve of the subject. The method can also include stimulating the vagus nerve of the subject with the vagus nerve stimulation system, based on the determination that the subject has the intracranial hemorrhage.

Some non-limiting examples of the disclosure provide a method for decreasing the level of matrix metalloproteinase-9 ("MMP-9") in subject. The method can include positioning a vagus nerve stimulation system on the subject, the vagus nerve stimulation system being configured to provide an electrical stimulation to the vagus nerve of the subject, and stimulating the vagus nerve of the subject with the vagus nerve stimulation system to decrease the level of MMP-9 in the brain of the subject.

Some non-limiting examples of the disclosure provide a treatment system. The treatment system can include a vagus nerve stimulation system. The vagus nerve stimulation system can include a first electrode, a second electrode, a first processor, and a signal generator in communication with the first electrode, and the second electrode, and the first processor. The signal generator can be configured to emit an electrical waveform to the first electrode and the second electrode to provide an electrical stimulation to the vagus nerve of the subject. The treatment system can include a computer system being in communication with the vagus nerve stimulation system, the computer system having a second processor, the second processor can be configured to receive imaging data acquired by an imaging system, the imaging system being from a head of the subject. Determine that the subject has an aneurysm from the imaging data, and transmit a signal to the vagus nerve stimulation system, the signal can enable the vagus nerve stimulation system to provide the electrical stimulation to the vagus nerve of the subject, via the signal generator.

Some non-limiting examples of the disclosure provide a method for decreasing a matrix degrading enzyme in a subject. The method can include positioning a vagus nerve stimulation system on the subject, the vagus nerve stimulation system can be configured to provide an electrical stimulation to the vagus nerve of the subject, and stimulating the vagus nerve of the subject with the vagus nerve stimulation system to decrease the level of the matrix degrading enzyme in the brain of the subject.

BRIEF DESCRIPTIONS OF THE DRAWINGS

DETAILED DESCRIPTION

Figure 1:
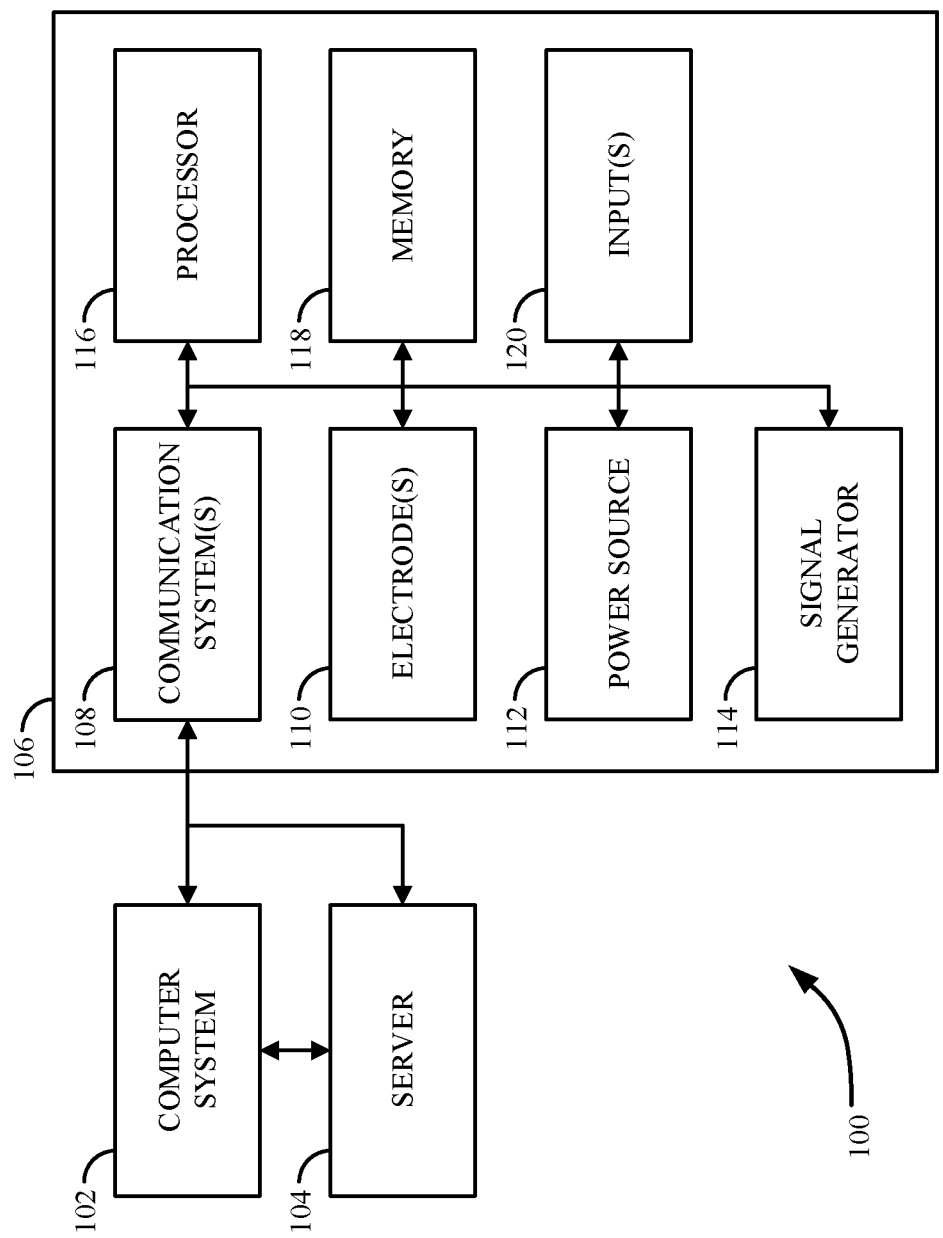
FIG. 1 is a schematic illustration of an aneurysm treatment system, which includes a non-invasive vagus nerve stimulation system in accordance with the present disclosure.

In some non-limiting examples, aspects of the present disclosure, including computerized implementations of methods, can be implemented as a system, method, apparatus, or article of manufacture using standard programming or engineering techniques to produce software, firmware, hardware, or any combination thereof to control a processor device, a computer (e.g., a processor device operatively coupled to a memory), or another electronically operated controller to implement aspects detailed herein. Accordingly, for example, non-limiting examples of the invention can be implemented as a set of instructions, tangibly embodied on a non-transitory computer-readable media, such that a processor device can implement the instructions based upon reading the instructions from the computer-readable media. Some non-limiting examples of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the invention. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, the term, "controller" and "processor" include any device capable of executing a computer program, or any device that includes logic gates configured to execute the described functionality. For example, this may include a processor, a microcontroller, a field-programmable gate array, a programmable logic controller, and the like.

The following discussion is presented for a person skilled in the art to make and use non-limiting examples of the invention. Various modifications to the illustrated non-limiting examples will be readily apparent to those skilled in the art, and the generic principles herein can be applied to other non-limiting examples and applications without departing from non-limiting examples of the invention. Thus, non-limiting examples of the invention are not intended to be limited to non-limiting examples shown, but are to be accorded the widest scope consistent with the principles and features disclosed herein. The following detailed description is to be read with reference to the figures, in which like elements in different figures have like reference numerals. The figures, which are not necessarily to scale, depict selected non-limiting examples and are not intended to limit the scope of non-limiting examples of the invention. Skilled artisans will recognize the examples provided herein have many useful alternatives and fall within the scope of non-limiting examples of the invention.

Generally, hemorrhagic stroke (which includes SAH) is form of intracranial hemorrhage, characterized according to the anatomical location. Intraparenchymal or intracerebral hemorrhage results from bleeding in the brain parenchyma, while SAH is the result of bleeding within the membranes overlying the brain (e.g., specifically in the subarachnoid space between the pia and the arachnoid membranes). Alternatively, a subdural hematoma is an example of a non-stroke intracranial bleeding.

As detailed above, SAH is a life-threating condition, necessitating immediate pharmaceutical and surgical intervention. Although swift intervention may mitigate or prevent complications that would significantly impact the patient's quality of life (e.g., brain damage), other complications can persist, and surgical interventions may not happen quick enough. For example, in some cases, after the onset of SAH related symptoms, the patient may be located much too far away from a hospital to prevent any detrimental complications. Due to the time-sensitive nature of SAH and extreme severity of the associated complications, it is not surprising that the prognosis for this condition is highly variable. In fact, it is estimated that one-third of patients with SAH will die from the condition, one-third of patients with SAH will survive and be in a relatively good condition, while the remaining third of patients with SAH will survive, but will have lasting disabilities. The problems associated with the third of SAH patients having lasting disabilities, are also highly variable. For example, these problems can be short-term or long-term and can include, speech and language issues, weakness or paralysis, visual problems, seizures, fatigue, headaches, memory loss, concentration problems, personality changes, and so on.

The incidences of SAH represent a significant source of morbidity and mortality resulting from vascular conditions. In fact, among the conditions that cause morbidity and mortality, SAH represents a significant slice. Crude incidence rates of SAH estimate a range of 2 to 16 for every 100,000 persons in the world, every year. In the United States alone, the statistic is inflated, where the incidence rate of SAH ranges from 9.7 to 14.5 for every 100,000 persons, every year. The mean fatality rate for a given case of SAH after hospitalization is 32% (for the United States), while it is also estimated that nearly 12% of patients die before even reaching a hospital. Additionally, half of those that survive SAH, suffer from permanent neurological or cognitive deficits, and fail to return to premorbid level of function.

Generally, the vast majority of SAH cases (85%) are caused by rupturing of an intracranial aneurysm. Unfortunately, current treatments for aneurysmal rupture (and SAH) have limited efficacy. For example, once ruptured, surgical or endovascular intervention is deployed to secure the aneurysm, and prevent further bleeding. However, treatments aside from treating the rupture are focused on life saving interventions, which are unrelated to the aneurysm. This is not surprising, at least because of the abruptness of the condition. In other words, patients may be seemingly fine one day, while the following day present rupturing and bleeding into the sub arachnoid space.

Considering that most cases of SAH stem from a ruptured aneurysm, the course of action for newly discovered aneurysms may appear crude. However, following current knowledge, conventional approaches do have a purpose. For example, suppose during a routine imaging procedure, a budding aneurysm is serendipitously discovered. In this case, where the unruptured intracranial aneurysm is <10 millimeters (e.g., for the largest diameter) and lacks high-risk features, surgical intervention is not deployed, as the likelihood to inadvertently rupture the aneurysm is relatively high (which can cause a cascade of associated complications). Thus, conventionally, surgical intervention is not deployed, and the patient has to deal with the consequences that the detected aneurysm may burst at any moment. While surgical intervention is not utilized, current guidelines on the management of intracranial aneurysms recommend risk factor reduction, and a wait-and-see approach with periodic follow up imaging studies. However, a subset of unruptured aneurysms eventually grow in size or rupture, which can occur without associated growth. As such, generally, even when an aneurysm is discovered, nothing substantial can be done to treat the aneurysm other than invasive surgical procedures which carry significant risk. In fact, currently, there is no strong predictor of aneurysm growth or rupture in the majority of patients. Unfortunately, as indicated above, these patients are forced to live with the burden that SAH may happen at any moment. Outside of risk factor reduction, there is no direct treatment known to prevent aneurysm formation, growth and rupture.

As discussed above, SAH can cause a non-ischemic stroke, and thus SAH is generally accepted as being a subset of a stroke that is medically distinct from ischemic stroke. Thus, stroke can be divided into two main categories that are medically distinct: (1) hemorrhagic stroke, and (2) ischemic stroke. Each of these categories have vastly different pathophysiology characteristics. The first, hemorrhagic stroke (including SAH), is a complicated grouping. Generally, one or more blood vessels ruptures or is severed, causing massive bleeding on or into the brain. This causes normal blood flow to be impeded for areas distal to the rupture site (e.g., away or downstream from the bleeding site). The lack of normal blood flow can cause loss of function to these areas, or permanent damage (e.g., from insufficient oxygenation). Additionally, the mere presence of blood leaking into the brain causes massive complications, such as, for example, increased pressure on the brain tissue, and the initiation of multiple inflammatory cascades. Conversely, the second, ischemic stroke, is defined by the lack of sufficient blood flow to an area of the brain, which can cause dying of the brain tissue within the area (e.g., due to lack of oxygen). Ischemic stroke is caused by conditions that yield insufficient blood supply, systemically or localized (e.g., a clot occluding a brain blood vessel). For example, ischemic stroke can be caused by a thrombosis (e.g., a blood clot in a brain blood vessel), an embolism, a general decrease in blood supply (e.g., from shock), and the like.

Treating a potential or actual rupture of a vessel is entirely different than treating an occluded vessel. One presents with hemorrhage and the ramifications of uncontrolled bleeding, whereas the other presents with restricted or occluded blood flow and the ramifications of a lack of blood flow through the occluded vessel. Although ischemic stroke can be caused by various conditions, typical treatment regimens generally follow a similar protocol, aiming to drive increased blood flow to the particular region of the brain (e.g., increase blood pressure, cardiac output, dissolve the clot, and the like).

Not surprisingly, typical treatment regimens for ischemic stroke are far different and generally do not overlap, when compared to typical treatment regimens for hemorrhagic strokes. Generally, interventions for ischemic stroke aim to restore blood flow, or preserve brain tissue. Alternatively, therapies for intracerebral hemorrhage may include the targeting (or suppression) of the cascade of events triggered by the presence of substantial volumes of blood within the parenchyma of the brain. Thus, due to the vastly different pathophysiology, ischemic stroke therapies are generally understood to have no utility for intracranial hemorrhage (including SAH).

Therapies between ischemic and hemorrhage strokes are entirely separate, and in some cases, a treatment typical for one group can be detrimental when applied to the opposing group. More specifically, therapies potentially effective for ischemic strokes may be ineffective or even dangerous for hemorrhagic strokes (or vice versa). For example, blood clot dissolving drugs (e.g., tissue plasminogen activator, tPA) have proven to be effective in treating forms of ischemic stroke that are caused by blood clots. However, administration of clot-dissolving drugs for a hemorrhagic stroke (including SAH) would not only fail to address the hemorrhage, but could also detrimentally enhance or extend bleeding through the aneurysm space. Thus, conventionally, interventions for ischemic strokes are not used for hemorrhagic strokes, at least because they fail to address, and can worsen, the problem.

Recently, some have contemplated the usage of vagus nerve stimulation ("VNS") to treat an ischemic stroke. In these instances, a pair of electrodes (or a system capable of implementing the following functionality) is used to electrically excite the vagus nerve of the patient (e.g., by applying a voltage across the electrodes). In these instances, stimulation of the vagus nerve was completed non-invasively, which can be encapsulated by the previously coined term ("nVNS"). These efforts taught that nVNS should be used following the diagnosis of an ischemic stroke, with the aim being to drive blood to the impacted region of the brain and reduce the damage caused by reduced blood flow. Considering that nVNS was found to increase levels of norepinephrine, the aim of driving blood to the impacted region was at least partially fulfilled. For example, typical intervention following a stroke is to raise blood pressure and increase cardiac output (which includes heart rate), to drive blood to the region of tissue seeing reduced blood flow. Thus, not surprisingly, considering that higher levels of norepinephrine increase both heart rate and blood pressure (required for typical ischemic stroke protocol), the nVNS fulfilled its aim.

Although nVNS has been contemplated for usage for ischemic strokes, nVNS has not been contemplated for usage for the other branch of strokes, including hemorrhagic strokes. This is logical given the seemingly-detrimental repercussions of using a treatment for ischemic stroke shown to be effective to increase blood flow (increase norepinephrine) in the context of an aneurism or hemorrhage.

Contrary to conventional understanding of treating aneurysm or hemorrhage (including SAH), the present disclosure has created systems and methods that improve the outcome of patients with hemorrhagic stroke (including SAH) using nVNS. The present disclosure provides systems and methods for nVNS (or VNS) that can be utilized to treat an aneurism or a rupture, to thereby improve survival rates, and reduce neurological dysfunction resulting from SAH. In other words, the disclosure counterintuitively provides systems and methods where nVNS (or VNS) can be used such that the benefits to the patient outstrip any presumptive drawbacks.

Additionally, some non-limiting examples of the disclosure provide systems and methods are provided that utilize nVNS (or VNS) to prevent or delay aneurysm formation, growth, and rupture. As described above, conventionally, when an aneurysm is found, a wait-and-see approach is utilized where routine follow-up images are taken to monitor potential changes in the aneurysm shape or size. However, in some cases, the aneurysm can rupture during this wait-and-see period. Thus, some non-limiting examples of the disclosure provide systems and methods that change conventional treatments strategies by utilizing nVNS (or VNS) to prevent further aneurysm growth (or change in shape), and decrease the risk of aneurysm rupture. Considering that the prevalence of unruptured intracranial aneurysms in the general population is estimated to be 3.2%, there exists an unmet need for improved systems and methods for treating intracranial aneurysms, and for bettering patient outcomes following aneurysm rupture.

FIG. 1 shows an example of an aneurysm treatment system 100, according to some non-limiting examples of the disclosure. The aneurysm treatment system 100 includes a computer system 102, a server 104, and an nVNS system 106. The computer system 102, can embody many different forms. For example, the computer system 102 can include typical components used in the art to facilitate functionality of the computer system 102 (e.g., a processor, memory, a communication system, user interface(s), and the like.). The computer 102 may include a display, an input device, a keyboard, a mouse, a graphical user interface, a touch-screen display, and so on. The computer system 102 may be a mobile computing device. The computer system 102 is shown being in communication (e.g., wired, wireless, serial) with the server 104, and a communication system 108 of the nVNS system 106 (e.g., by using a communication system of the computer system 102).

The server 104 can also embody many different forms, as typically used in the art. For example, the server 104 can include processors (e.g., central processing units, graphics processing units, and the like), and communication systems. The server 104 is shown in FIG. 1 as being in communication with the computer system 102 and the nVNS system 106 (e.g., via the communication system 108). Thus, in some non-limiting examples, the server 104 can send and receive data among the components in communication, and as such, can instruct (or cause) the computer system 102 and the nVNS system 108 to implement specific functionalities (e.g., receive sensor data, store sensor data, transmit sensor data, provide a stimulation, and the like).

In the illustrated non-limiting example of FIG. 1, the nVNS system 106 includes the communication system 108, electrodes 110, a power source 112, a signal generator 114, a processor 116, memory 118, and input(s) 120. As previously discussed, the communication system 108 allows communication between the nVNS system 106 and other systems (e.g., the computer system 102, the server 104, and the like.). The communication system 108 can include any suitable hardware, firmware, and/or software for communicating with the other systems, over any suitable communication networks. For example, the communication system 108 can include one or more transceivers, one or more communication chips and/or chip sets, and the like. In a more particular example, communication system 108 can include hardware, firmware and/or software that can be used to establish a coaxial connection, a fiber optic connection, an Ethernet connection, a USB connection, a Wi-Fi connection, a Bluetooth connection, a cellular connection, and the like.

The nVNS system 106 also includes electrodes 110. The electrodes 110 can be typically structured as known in the art. For example, the electrodes 110 can include metal plates (e.g., stainless steel, platinum, or a platinum-iridium alloy, and the like), and are electrically connected to the signal generator 114. This way, when the signal generator 114 electrically excites the electrodes 110, for example, by the application of a voltage signal, current signal, and the like, the electrodes 110 thereby provide a current from one electrode, through a conduction medium (e.g., a subject), and into another electrode. In some non-limiting examples, the electrical signal may be a direct current ("DC") form of the signal, an alternating current ("AC") form of the signal, a pulsed signal (e.g., an impulse, a rectangular pulse), and the like In some cases, the electrodes 110 can include two, three, four, separate electrodes, while in other cases, the electrodes 110 can include multiple pairs of electrodes, where each pair can be individually electrically excitable by the signal generator 114.

In an alternative non-limiting example, the electrodes 110 can be implemented as magnetic coils (e.g., a toroidal coil) with a corresponding electrically conducing medium. More specifically, a given magnetic coil can be surrounded by the electrically conducing medium (e.g., a metal, such as stainless steel) that supports and conducts a current. Generally, when the signal generator 114 applies an electrical signal to the magnetic coils, the magnetic field generated by the magnetic coils (e.g., a time varying magnetic field), induces a current through the first conducting medium of the first magnetic coil, through the conduction medium (e.g., the subject), and through the second conducting medium of the second magnetic coil.

As shown in the illustrated non-limiting example of FIG. 1, the power source 112 supplies power to all of the components within the nVNS system 106. Thus, generally, the power source 112 can embody many different forms. For example, the power source 112 can be a hardwired connection (e.g., a Universal Serial Bus connection), or it can be an electrical storage device (e.g., a battery). In one specific non-limiting example, the power source 112 can be a rechargeable battery, which can be charged via connection with an external power transformer (or other wired connection). As implied above, the power source 112 supplies power to the signal generator 114, which then provides an electrical excitation signal to the electrodes 110. The signal generator 114 generally includes components necessary to generate the electrical signals. Thus, for example, the signal generator 114 can include a processor, memory, oscillators, digital to analog converters ("DAC"), and the like. In some non-limiting examples, the signal generator 114 can be instructed (e.g., by the processor 116) to adjust specific parameters related to the electrically excitable signal sent to the electrodes 110. These specific parameters can include, for example, adjustments in waveforms, frequency, pulse width, duty cycle, amplitude, number of impulses, and the like.

The processor 116 generally controls the functionality of the nVNS system 106, and can embody different forms. For example, the processor 116 can be any suitable hardware processor or combination of processors, such as a central processing unit ("CPU"), a graphics processing unit ("GPU"), and the like, which can execute a program (e.g., retrieved from memory 130). The program can include the processes described below.

In some non-limiting examples, the memory 118 can include any suitable volatile memory, non-volatile memory, storage, or any suitable combination thereof. For example, the memory 118 can include random-access memory ("RAM"), static random-access memory ("SRAM"), read-only memory ("ROM"), electrically erasable programmable read-only memory ("EEPROM"), one or more flash drives, one or more hard disks, one or more solid state drives, one or more optical drives, and the like. In some non-limiting examples, the memory 118 can have encoded thereon a computer program for controlling operation of the processor 116.

The inputs 120 of the nVNS system 106 can include indicators, sensors, actuated buttons, and the like. For example, the inputs(s) 120 can include an actuated button that when depressed, causes the signal generator 114 to emit the electrically signal to the electrodes 110 (e.g., as long as the actuated button is depressed by a user). As another example, the inputs 120 of the nVNS system 106 can include physiological sensors, such as, for example, electrocardiogram ("ECG") electrodes, heart rate monitors, and the like.

In some non-limiting examples, the components of the nVNS system 106 can be incorporated within a single unit, while in other cases, the nVNS system 106 can include separable components. For example, in some non-limiting examples, the electrodes 110 and signal generator 114 may be separated from the remaining components, while in other non-limiting examples, all of the components within the nVNS system 106 can be mounted and secured within a housing.

Figure 2:
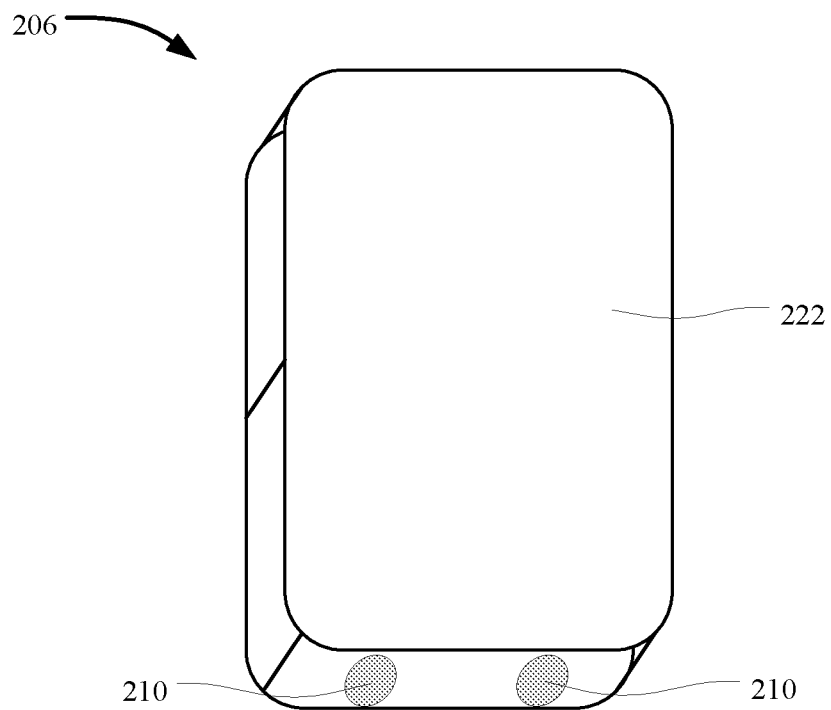
FIG. 2 is an illustration of a perspective view of another non-invasive vagus nerve stimulation system, which is a specific non-limiting example of the vagus nerve stimulation system of FIG. 1.
Figure 3:
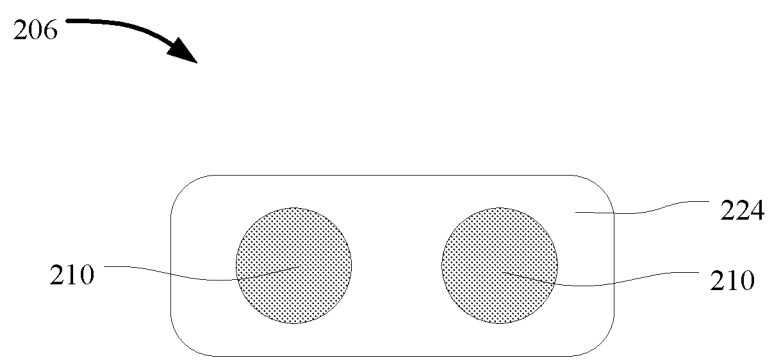
FIG. 3 is an illustration of a top side view of the vagus nerve stimulation system of FIG. 2.

FIGS. 2 and 3 show an example of another nVNS system 206, which is a specific implementation of the nVNS system 106. More specifically, the nVNS system 206 also includes a communication system 208, electrodes 210, a power source 212, a signal generator 214, a processor 216, memory 218, and inputs 220. The communication system 208, the power source 212, the signal generator 214, the processor 216, memory 218, and the inputs 220 have been removed for clarity of representation. However, considering that the nVNS system 206 is a specific implementation of the nVNS system 100, the previous discussion of the nVNS system 106 also pertains to the nVNS system 206. As shown in the illustrated non-limiting example of FIGS. 2 and 3, the nVNS system 206 is packaged within a rectangular housing 222 to stabilize and secure the components within the nVNS system 206. In alternative non-limiting examples, the housing 222 may have alternative shapes (e.g., circular, trapezoidal, triangular, and the like). The housing 222 includes a bottom surface 224 having apertures that receive the electrodes 210. Although the electrodes 210 are shown as being equidistant from a central midline of the bottom surface 224, in alternative non-limiting examples, the electrodes 210 can be separated by differing distances.

Figure 4:
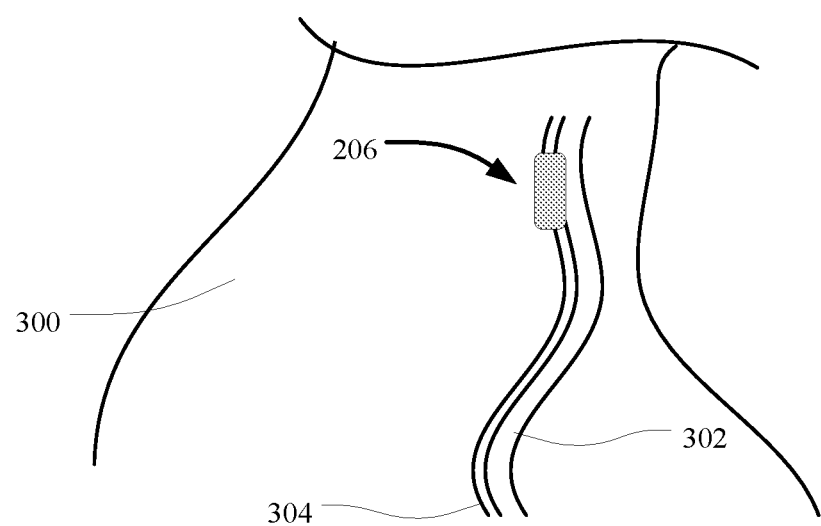
FIG. 4 is an illustration of the vagus nerve stimulation system of FIG. 2 providing electrical stimulation to the vagus nerve of the patient.

FIG. 4 shows an illustration of the nVNS system 206 providing electrical stimulation to the subject 300. In some non-limiting examples, a doctor (or other practitioner) may prescribe a treatment, which uses the nVNS system 206. Then, the doctor, other practitioner, or in some cases the subject, can use the nVNS system 206 to perform the prescribed stimulation treatment. As shown in FIG. 4, the electrodes 210 of the nVNS system 206 are placed in contact with the skin of the neck 300 of the subject. More specifically, the electrodes 210 of the nVNS system 206 are placed, such that they are aligned with the vagus nerve 304, where the vagus nerve 304 is situated adjacent to the carotid artery 302 of the subject 300. Once the nVNS system 206 is sufficiently placed, the user (or automatically via a transmitted signal) can cause the nVNS system 206 (e.g., by actuation of a button) to electrically excite the electrodes 210. Alternatively, VNS can be delivered via the external ear canal.

Figure 5:
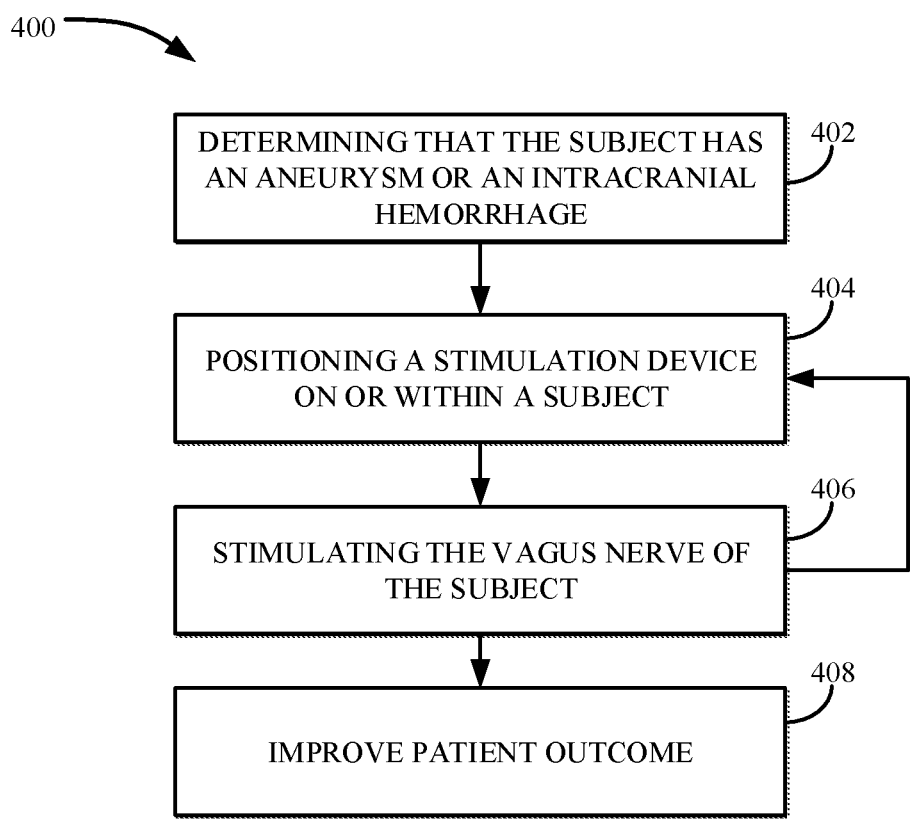
FIG. 5 is a flowchart of a process for improving patient outcome in accordance with the present disclosure.

FIG. 5 is an example of a process 400 for improving the patient outcome, which relates to the previously described systems and components. Process 400 includes at step 402, determining that the subject has an aneurysm or an intracranial hemorrhage (including SAH). In some cases, a doctor (or other practitioner) can view an image (e.g., of a user's head) derived from imaging data from an imaging system (e.g., CT, MRI, digital subtraction angiography (DSA), ultrasound, and the like) on a display of a computer system (e.g., the computer system 102). The doctor can then analyze the image to determine if the subject has an aneurysm If the doctor determines that the subject has an aneurysm, the doctor may subsequently indicate the presence of the aneurysm by initiating a user selection (e.g., via an interaction with a display and a user input of the computer system). In some cases, the user selection may cause a patient health record to be updated with the information. In other cases, the user selection can be transmitted to a vagus nerve stimulation system (e.g., the nVNS system 106) to enable the vagus nerve stimulation system to provide the electrical stimulation.

In some non-limiting examples, the process 400 at 402 can determine that the subject has an intracranial hemorrhage (including SAH). Similarly, the determination of the aneurysm above, in some cases, a medical image of the subject's head can be analyzed to determine that the subject has an intracranial hemorrhage. For example, the medical image may show blood pooling, or a formation of a blood clot within the brain. In other cases, the intracranial hemorrhage can be determined by determining an intracranial pressure. For example, a catheter system (including a pressure sensor) may be directed into the intracranial cavity of the subject to measure an intracranial pressure. Then, the measured intracranial pressure can be compared to a threshold intracranial pressure to determine whether or not the subject has an intracranial hemorrhage (e.g., if the measured pressure is greater than or equal to the threshold pressure). In some non-limiting examples, the determination of blood in the cerebrospinal fluid ("CSF") can be indicative of an intracranial hemorrhage. For example, a doctor (or other practitioner) can obtain cerebrospinal fluid (e.g., by a lumbar puncture) to determine if blood resides in the CSF. Then, if blood is detected in the CSF (or a particular amount of blood) the doctor can determine that the subject has an intracranial hemorrhage.

Regardless of the diagnosis of an aneurysm or intracranial hemorrhage, process 400 can proceed to step 404. At 404 process 400 can include positioning a stimulation device on or within the subject. The stimulation device can embody many forms as typically used in the art. For example, the stimulation device can include a signal generator (or electrical impulse generator) in electrical communication with two or more electrodes. The electrodes can either be surface electrodes (e.g., the skin surface), or in other cases, can be implantable electrodes (e.g., implanted in the skin, and the like). The electrodes are positioned on or within the subject, such that they are in close proximity to the vagus nerve. As a specific example, in the case of surface electrodes, the electrodes are placed (and adhered) on the skin surface over the vagus nerve. In some non-limiting examples, the stimulation device can be the nVNS systems 106, 206, where the specific nVNS system is placed (and pressed) on the subject (e.g., as shown in FIG. 4).

Once sufficiently placed, the stimulation device can stimulate the vagus nerve of the subject at step 406 of process 400. In some cases, a button must be actuated to cause the stimulation device to emit the electrical stimulation to the vagus nerve. As discussed above, in some implementations where the stimulation system is locked, even if the button is actuated, no electrical stimulation will occur. In some non-limiting examples, the electrical stimulation is caused by the emitting of an electrical waveform from a signal generator to the electrodes (or other suitable constructions, for example, the magnetic coils discussed previously). The electrical waveform can have a frequency in a frequency range (e.g., 1 Hz to 10 kHz, 3 kHz to 7 KHz, and the like), while in some cases the frequency can be a single frequency (e.g., 5 kHz, 25 Hz, and the like). In some cases, the electrical waveform can be a rectangular waveform, a sinusoid waveform, a saw tooth waveform, combinations of sinusoids, and the like, having various DC values (e.g., centered around 0, 1, 2, 3, and the like). The electrical waveform can also have a pulse width in a range (e.g., 1 microsecond to 1 second, 0.1 milliseconds to 10 milliseconds, and the like), while in other cases, the pulse width can be a single value (e.g., 1 millisecond).

In one non-limiting example, the electrical stimulation may be formed as a sinusoidal wave, which is bipolar (e.g., oscillating about 0 DC value, such that positive and negative portions of the sinusoidal wave exist). The sinusoidal wave causes bidirectional stimulation (e.g., along a first axial direction, and along a second opposite axial direction to the first axial direction). The direction of application and the stimulus parameters (amplitude, frequency, stimulus duration, treatment repetition such as number of stimulations per hour or day, side of stimulation such as right, left or alternating bilateral, duration of treatment as in hours, days, weeks) are selected based on treatment requirements.

In some non-limiting examples, the electrical waveform can be applied for a duration, which can cause the electrical stimulation of the vagus nerve to be applied for the duration. The duration can be two minutes, five minutes, and the like. FIG. 5 also shows an arrow extending out from step 406 and back to step 404, implying that after completion of the stimulation of the vagus nerve, the user can reposition, while in other cases, simply wait a period of time (a duration) before stimulating the vagus nerve again. In some therapy regimens, stimulation of the vagus nerve (e.g., at step 406) can be repeated daily, for a week (or weeks, or a number of days), a month (or months), a year, and the like. In other therapy regimens, the user may stimulate the vagus nerve until symptoms of their (or the subject's) corresponding disease state vanish. In other words, the user may stimulate the vagus nerve daily (twice daily, three times daily, and the like), until their symptoms go away or decreases in severity below a threshold (e.g., intracranial pressure decreases, related to an intracranial hemorrhage, or the aneurysm decreases in size or vanishes).

After stimulation of the vagus nerve at step 406, process 400 can proceed to step 408. At 408, stimulation of the vagus nerve improves the patient outcome. As an example, in the case of the subject having an aneurysm, stimulation of the vagus nerve (e.g., once or a number of times) can prevent further growth of the aneurysm, and can decrease the likelihood that the aneurysm ruptures. Additionally, according to some non-limiting examples of the disclosure, it has been shown that stimulation of the vagus nerve decreases the level (and expression) of matrix metalloproteinase-9 ("MMP-9"), which may contribute to the cessation of growth of the aneurysm, and decreased likelihood of aneurysm rupture. More specifically, with decreased gene expression of MMP-9 (decreased levels of mRNA corresponding to MMP-9), translation of the MMP-9 mRNA decreases, thereby decreasing the levels of MMP-9 in the subject (e.g., in the blood stream, within a blood vessel of the brain, within brain tissue, and the like). As another example, in the case of the subject having an intracranial hemorrhage, which may be caused by a ruptured aneurysm, according to some non-limiting examples of the disclosure, it is shown that stimulation of the vagus nerve increases the likelihood that the subject survives, and in the case of survival, improves potential neurological deficits. More specifically, when the aneurysm of the subject ruptures, non-limiting examples of the disclosure show decreased effects of the rupture. These decreased effects of the rupture include, an increased likelihood of survival, decreased neurological deficits, improved quality of life, etc.

As indicated above, steps within process 400 can repeat. For example, while the subject is implementing the stimulation therapy regimen (e.g., stimulation to the vagus nerve daily), the subject can be imaged again to determine if, or the extent, of how the aneurysm has changed size or shape.

Examples

The following examples have been presented in order to further illustrate aspects of the disclosure, and are not meant to limit the scope of the disclosure in any way.

SAH is a devastating disease with very high acute mortality rates and persistent neurological deficits in survivors. Inflammation can contribute to intracranial aneurysm formation, growth, destabilization, and rupture, as well as outcome after rupture, both in humans and in experimental models. As described herein, systems and methods are provided for VNS as a neuromodulation technique that can reduce inflammation. However, the need for surgical implantation of electrodes around the vagus has thus far limited the clinical applications of VNS. Recently, noninvasive VNS techniques with an excellent safety and tolerability profile have been developed and approved for clinical use for neurological indications.

We, therefore, tested a novel noninvasive cervical transcutaneous VNS approach in a mouse model of intracranial aneurysm formation and rupture that recapitulates the clinical features as well as the inflammatory mechanisms. We examined clinically relevant acute outcome end points including rupture rate and survival after rupture using 2 different levels of model severity. In summary, the data strongly suggests that chronic daily VNS inhibits aneurysm rupture and reduces matrix metalloproteinase-9 ("MMP-9") expression as one mechanism. Post rupture survival is also improved by VNS regardless of the degree of SAH.

Methods

Experiments were conducted in accordance with the Guide for Care and Use of Laboratory Animals (NIH Publication No. 85-23, 1996) and approved by the Massachusetts General Hospital Institutional Animal Care and Use Committee. Experimental protocol and timelines are summarized in FIG. 6.

Intracranial Aneurysm Model

Intracranial aneurysms were induced using intracranial elastase injection combined with systemic deoxycorticosterone acetate-salt hypertension in mice (8 to 10-week-old, male, C57BL/6; Charles River Laboratories, Wilmington, MA), as described previously with minor modifications (see, e.g., FIG. 6). All mice underwent unilateral nephrectomy. One week later, a deoxycorticosterone acetate pellet (66 mg, 28-day release; Innovative Research of America, Sarasota, FL) was implanted, and 1% NaCl was added to drinking water to induce systemic hypertension. A single dose of elastase (35 mU; E7885, porcine pancreatic elastase, lyophilized powder, 20 mg; Sigma Aldrich, St. Louis, MO) was stereotaxically injected into the right basal cistern (2.6 mm posterior, 1.5 mm lateral, and 5.7 mm ventral to bregma) after a midline scalp incision under isoflurane anesthesia (3% induction, 1% maintenance, in 30% $O_2$ and 70% $N_2O$).

A separate cohort of mice (severe model) additionally received high-salt diet (0.39% NaCl) and supplemental doses of deoxycorticosterone acetate powder (34 mg every other day subcutaneously, in 0.1 mL olive oil) for higher mean arterial pressures (e.g., see FIG. 6) and worse outcomes. In the mild model, blood pressures ("BPs") were measured via a femoral artery catheter under general anesthesia (isoflurane 2.5% induction, 1% maintenance in 70% $N_2O$ and 30% $O_2$) at the time of euthanasia. In the severe model, mortality and morbidity were high and significantly differed between VNS and femoral nerve stimulation ("FNS") groups, precluding measurements just before euthanasia. Therefore, in the severe model, we measured the BPs using the same method, but on day 5 in a separate dedicated cohort that has undergone identical procedures.

Vagus

The day after elastase injection, animals were randomly assigned to either right transcutaneous (cervical) VNS or transcutaneous (inguinal) FNS groups. We selected FNS because we aimed (1) to control for any potential effects of cutaneous stimulation and muscle twitching, (2) to avoid an autonomic nerve that may have effects of its own, and (3) to stay away from the cervical region to avoid inadvertent vagus stimulation in this small species. The stimulus consisted of 1-ms pulses of 5 kilohertz ("kHz") sine waves, repeated at 25 Hz, for 2 minutes (e.g., 25 times of the 5 kHz pulse over two minutes), delivered twice, 5 minutes apart (see, e.g., FIG. 1A) using custom-made bipolar stimulation electrodes connected to the gammaCore device (electroCore, Basking Ridge, NJ). For each transcutaneous stimulation session, we titrated the stimulus intensity to be just above the muscle twitch threshold (≈7-9 Volts ("V")), similar to that used in patients. This noninvasive VNS protocol has previously been shown to successfully activate the vagus nerve and has been efficacious in other animal models such as focal cerebral ischemia, pain, and spreading depression.

Stimulation was delivered once daily until euthanasia by placing the electrodes on the shaved skin on the right side under brief general anesthesia. In a separate cohort, we detected only a 12±3% decrease in BP and a 19±7% decrease in heart rate ("HR") during VNS, both of which started to recover even before the end of the 2-minute stimulation and completely resolved within 3 minutes. These mild and brief hemodynamic effects of VNS were unlikely to alter the course of aneurysm formation and rupture. More important for the latter, resting state BPs did not differ between VNS and FNS groups (see e.g., FIG. 6).

Outcome Measures

Two observers, one of whom was blinded to the treatment arm, performed neurological examinations daily. Neurological signs were graded as follows: 0, normal function; 1, reduced activity or weight loss>2 g of body weight (≈10% weight loss) for 24 hours; 2, flexion of the torso and forelimbs on lifting the animal by the tail; 3, circling to one side with normal posture at rest; 4, leaning to one side at rest; 5, no spontaneous activity; and 6, sudden spontaneous death. When mice developed severe signs (grades 4 or 5), they were euthanized. Because previous studies using this model showed that aneurysmal rupture occurs within 3 weeks of aneurysm induction, all remaining mice were euthanized 21 days after aneurysm induction. Before euthanasia, mean arterial pressures were measured via a femoral artery catheter under isoflurane anesthesia. After euthanasia, mice were transcardially perfused with 5 mL heparinized saline followed by 0.5 mL carbon black ink (0.1 mL/s). Brains were carefully removed to preserve the integrity of the circle of Willis and ventral surface imaged under a stereomicroscope for morphological changes. The majority of animals developed some degree of dolichoectasia and tortuosity (e.g., see FIG. 6) with increased diameters of the circle of Willis arteries; the latter was measured using a scale in view (e.g., see FIG. 6). Aneurysms were defined as localized outward bulging of the vascular wall, with the largest diameter greater than that of the parent artery. Aneurysms were often not filled with the dye indicating some degree of thrombosis. The number of aneurysms and the largest diameter of each aneurysm were quantified in each animal. SAH severity was graded as follows: 0, no hemorrhage; 1, localized hemorrhage, thin SAH; 2, multiple or broad hemorrhage, diffuse thick SAH; and 3, massive hemorrhage (see, e.g., FIG. 8).

In a separate cohort, we studied pro-inflammatory marker expression within the circle of Willis in a blinded fashion (n=6 each, VNS and FNS). Four days after the induction of aneurysms using the severe model as described above, we performed transcardiac saline perfusion and harvested the circle of Willis arteries. We measured mRNA expression of TNF-α (tumor necrosis factor-α), IL-1β (interleukin-1β), IL-6 (interleukin-6), iNOS (inducible nitric oxide synthase), MMP-9, and CCL2 (chemokine C-C motif ligand 2; also known as MCP-1 [monocyte chemotactic protein-1]), using reverse transcriptase polymerase chain reaction. Tissues were frozen in liquid nitrogen and kept in −80° C. freezer until RNA extraction. RNA was extracted using a commercial RNA extraction kit (Zymo Research, Irvine, CA) and converted to cDNA using a SuperScript III First-Strand Synthesis System kit (Invitrogen, Carlsbad, CA) according to manufacturer's instructions. Reverse transcriptase polymerase chain reaction was performed using TaqMan Gene Expression Assays and TaqMan Fast Advanced Master Mix (Applied Biosystems, Foster City, CA) with the following inflammatory marker primers: MMP-9, IL-1β, TNF-α, CCL2, IL-6, iNOS, and the housekeeping gene 18S. All primers were purchased from Applied Biosystems. Reverse transcriptase polymerase chain reaction was performed in a 7500 Fast Real-Time PCR system (Applied Biosystems, Foster City, CA) in triplicates. Relative mRNA expression levels were normalized to housekeeping gene.

Primary outcome end points were survival, deficit-free survival, deficit grade, rupture rate, and SAH grade. Secondary outcome end points were the presence or absence of tortuosity, circle of Willis artery diameters, and aneurysm counts, sizes and distribution. Pro-inflammatory marker mRNA expression was an exploratory end point. Sample sizes were chosen empirically (n=16/group for the mild model and n=14/group for the severe model) in the absence of prior experience with elastase technique in our lab. Mice were excluded if they failed to attain a target arterial BP of at least 95 mm Hg by induced-hypertension paradigm (n=6 FNS, 2 VNS in mild model), if they developed severe neurological deficits (grade 4-5) but without evidence of elastase effect on subsequent morphological examination (no tortuosity in any vessel, SAH, or aneurysm) suggesting unrelated cause (n=1 FNS and 1 VNS), and technical failure during elastase injection (n=3, before being assigned to a treatment arm). Only one animal was excluded in FNS group in gene expression experiment because of complete absence of tortuosity in any of the circle of Willis arteries, suggesting lack of elastase effect.

Statistical Analysis

All results were expressed as whisker-box plots (whiskers, full range; box, interquartile range; horizontal line, median; +, mean), mean±SEM, or as median (95% CI). Statistical testing was performed using Prism 6 (GraphPad Software, San Diego, CA). Individual statistical tests for each dataset are indicated in figure or table legends, or in text. P<0.05 was taken as statistical significance cutoff.

Results

The elastase plus induced-hypertension model led to aneurysm formation and spontaneous ruptures with various severities of SAH and neurological deficits. In the milder model, most animals survived the 21-day follow-up period (see e.g., FIG. 7, upper left), although some developed neurological deficits during the follow-up (see e.g., FIG. 7, lower left). Deficit-free survival tended to be higher (P=0.055; see e.g., FIG. 7, lower left) and neurological deficit grades milder (P=0.095; see e.g., FIG. 10, left) in the VNS group compared with the FNS (n=14 and 10, respectively). Maximum body weight loss did not differ between FNS and VNS groups in the mild model (6.1±0.9% versus 6.4±0.5%, respectively; unpaired t test). Postmortem examinations revealed gross morphological evidence for SAH, indicating aneurysmal rupture in 80% of animals in the FNS group (see e.g., FIG. 11, upper left). VNS significantly reduced rupture rates (29%; P=0.036). The relative risk of rupture was more than 3-fold higher in the FNS group compared with VNS (relative risk=3.6, CI [1.0-12.9]). SAH grades were also significantly lower in the VNS group (P=0.025; see e.g., FIG. 11, lower left). In contrast, aneurysm counts (see e.g., FIG. 12, upper left) did not differ between the groups. Although aneurysm diameters were statistically smaller in the VNS group (see e.g., FIG. 12, lower left), the magnitude of this effect was of uncertain biological significance. The center of gravity of aneurysm distribution did not differ between FNS and VNS groups (median [95% CI]: 1.61 mm [2.34–0.38 mm] lateral, 3.10 mm [4.01–1.12 mm] posterior, and 1.58 mm [2.20–0.87 mm] lateral, 2.96 mm [3.38–2.77 mm] posterior from bregma, for FNS and VNS, respectively; see e.g., FIG. 13, left). However, aneurysms developed farther from the injection site in FNS group compared with VNS (see e.g., FIG. 14, left).

Figure 9:
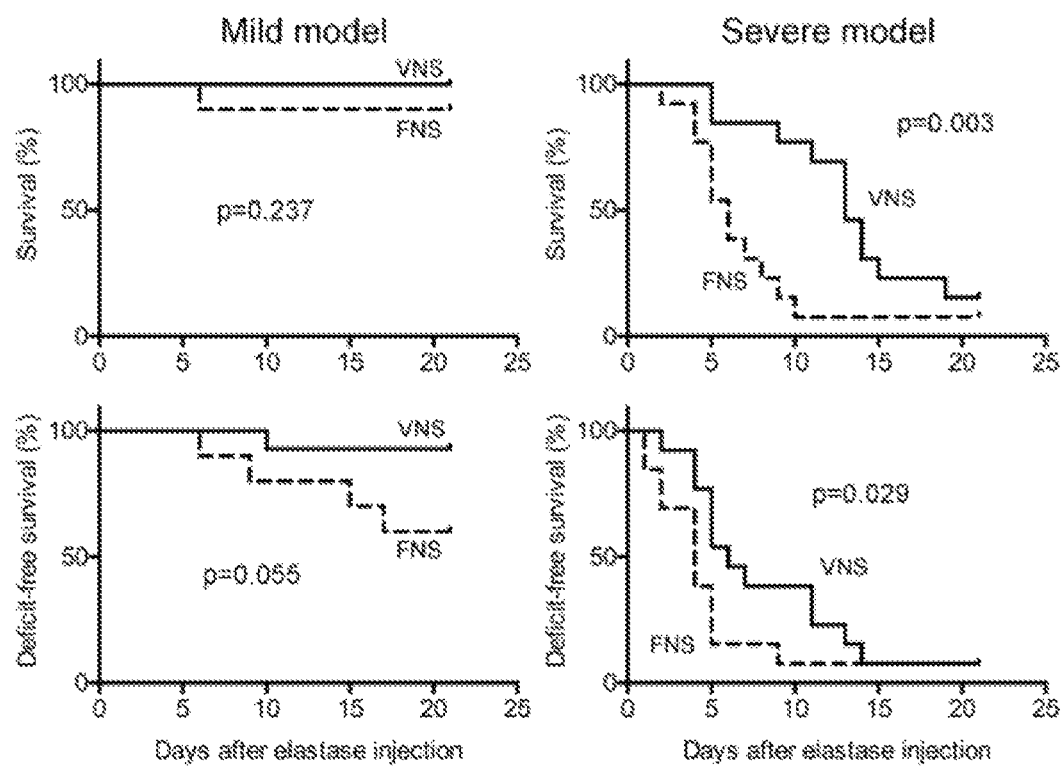
FIG. 9 is a series of charts showing the survival percentage, and the deficit-free survival percentage for both models, and between both groups (the femoral nerve stimulation group, and the vagus nerve stimulation group).
Figure 13:
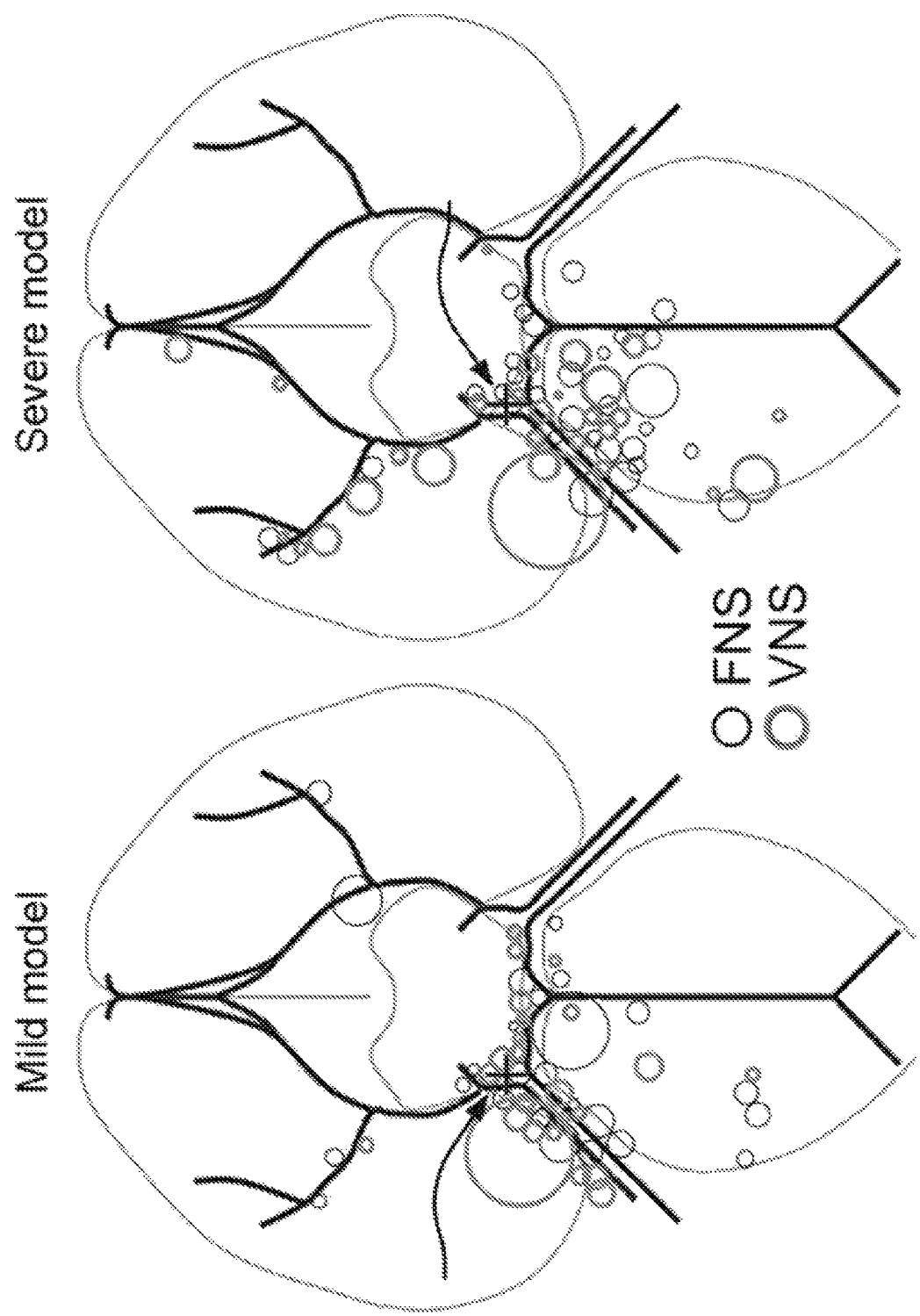
FIG. 13 is an illustration showing the distribution of aneurysms between the two models.
Figure 14:
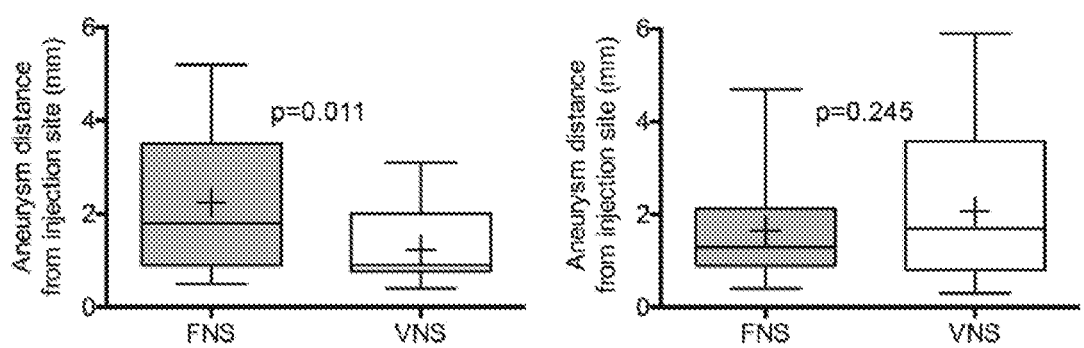
FIG. 14 is another series of graphs showing the aneurysm distance from the injection site for both models, and between both groups.

The severe model resulted in much higher mortality (P<0.001) and lower deficit-free survival rates (P<0.001) compared with the milder model in FNS controls (Gehan-Breslow-Wilcoxon test; see e.g., FIG. 9, left versus right). In the severe model, com-pared with FNS, VNS significantly improved survival (median survival 13 versus 6 days, respectively, n=13 each; P=0.003) and deficit-free survival rates (median deficit-free survival 6 versus 4 days, respectively, P=0.029), without affecting neurological deficit grades (see e.g., FIG. 10, right), rupture rates, or SAH grades (see e.g., FIG. 11, upper and lower right). Maximum body weight loss was similar between FNS and VNS groups (11.2±1.8% versus 10.2±1.3%, respectively; unpaired t test). Aneurysm counts or sizes (see e.g., FIG. 12, upper and lower right) also did not differ between FNS and VNS groups. Neither the center of gravity of aneurysm distribution (median [95% CI]: 1.31 mm [2.09–0.89 mm] lateral, 3.28 mm [3.91–2.76 mm] posterior, and 1.99 mm [2.19–1.61 mm] lateral, 3.03 mm [3.60–1.82 mm] posterior from bregma, for FNS and VNS, respectively; FIG. 13, right) nor the average distance of aneurysms from the injection site differed between the FNS and VNS groups (FIG. 14, right). Arterial diameters and presence of tortuosity in the circle of Willis also did not differ between FNS and VNS groups in either the mild or the severe model (Table), suggesting that VNS did not directly interfere with elastase effect.

After finding reduced rupture rates and improved survival after rupture in the VNS group, we also explored whether the anti-inflammatory effects of VNS may play a role. To this end, we measured the expression of pro-inflammatory mediators within the circle of Willis 7 days after elastase injection in the severe model. Expression was low in naïve circle of Willis (not shown). VNS generally suppressed the expression of all pro-inflammatory mediators compared with FNS (−34% WP-9, −21% IL-1β, −44% TNF-α, −25% CCL2, −28% IL-6, and −12% iNOS), although this effect reached statistical significance only for WP-9 in this exploratory cohort (n=5 and 6, FNS and VNS, respectively; see e.g., FIG. 15). Importantly, SAH grades in this cohort were mild and comparable between the groups (FNS, 1.20±0.20 and VNS, 1.00±0.26), suggesting that VNS suppressed the inflammatory response rather than SAH severity.

Discussion

Our data in an experimental intracranial aneurysm model with 2 levels of severity show that VNS reduces rupture rate in the mild version and improves post rupture survival and neurological deficits in the more severe version. We used 2 different model severities because neither alone allowed us to test all intended end points. Survival was nearly 100% in the mild model; therefore, the mild model did not allow us to assess VNS effect on survival. Conversely, nearly all animals developed a ruptured aneurysm in the severe model; therefore, the severe model did not allow us to assess rupture rates. Together, however, the 2 variations of the model complemented each other and independently yielded outcomes consistently favoring VNS.

Given the role of inflammation in aneurysm formation and growth, and the posited anti-inflammatory effects of VNS, suppression of inflammation, the present disclosure provides systems and methods for VNS action to reduce MMP-9 expression in macrophages and prevent aneurysm formation by suppressing inflammatory cytokines and MMP activity. For example, abdominal and/or thoracic aortic aneurysm formation may be prevented or treated. Thoracic aortic aneurysms may be treated, or other arterial aneurysms such as carotid or vertebral artery aneurysms may be treated. VNS has reduced the expression of MMP-9 in models of postmyocardial infarction remodeling and cardiac dysfunction as well. Although statistically not significant in our exploratory studies, suppression of other cytokines by VNS may also contribute. For example, TNF-α has been shown to play a critical role in aneurysm formation and rupture, and a reduction in CCL2 may suppress aneurysm growth and rupture by limiting macrophage infiltration. Of note, the gammaCore device that we used selectively stimulates the low-threshold, myelinated, afferents to the brain stem, rather than the high-threshold, non-myelinated, efferent C fibers. Vagal afferents project to nucleus tractus solitarius and from there to numerous subcortical neuro-modulatory nuclei, including the basal forebrain and locus ceruleus. Therefore, the central mechanisms of VNS action may also play a role in this model. Clearly, more studies are needed to elucidate the mechanisms of action of VNS on aneurysm growth and rupture and to dissect its molecular mediators.

Improved survival and deficits in the severe model despite comparable rupture rates and SAH grades strongly suggest that VNS has a protective effect on brain tissue as well. In massive ruptures, brain tissue suffers variable degrees of global ischemia because of a rise in intracranial pressure, as well as focal ischemia due to potential interruption of blood flow downstream to the ruptured vessel. VNS has uniformly improved outcomes in animal models of ischemic stroke, and anti-inflammatory mechanisms have been implicated as one mechanism. Therefore, it is possible that in addition to preventing aneurysm growth and rupture, VNS may improve outcome after SAH.

Although the elastase-hypertension model of intracranial aneurysms we used here is among the most widely used experimental models to examine aneurysm development and rupture, it does have caveats. One such caveat is the unpredictable timing of rupture and survival and deficits after a rupture. For example, sudden death because of massive SAH precludes ink perfusion for anatomic examination for aneurysms. Moreover, after massive SAH, ruptured aneurysms may clot or collapse, making them harder to identify. Therefore, it is likely that some aneurysms were undetected, which might explain the lack of differences in aneurysm counts or diameters between mild or severe models or between FNS and VNS groups. No doubt these data will have to be independently confirmed, preferably in more than one model, sex and species, and incorporating longer-term outcomes. However, given the outstanding safety and tolerability profile of noninvasive VNS, and easy bedside or ambulatory implementation, there is ample opportunity for rapid translation of these findings into clinical use. For example, chronic daily VNS can be used prophylactically to prevent aneurysm formation in patients with known propensity (e.g., fibromuscular dysplasia) or growth in patients with known unruptured aneurysms. Management of such patients is currently limited to follow-up neuroimaging only. In addition, VNS can also be used after rupture to improve SAH outcomes, which would be easy to implement at the bedside. Of course, more work is needed to determine the optimal therapeutic paradigms for these applications.

Figure 6:
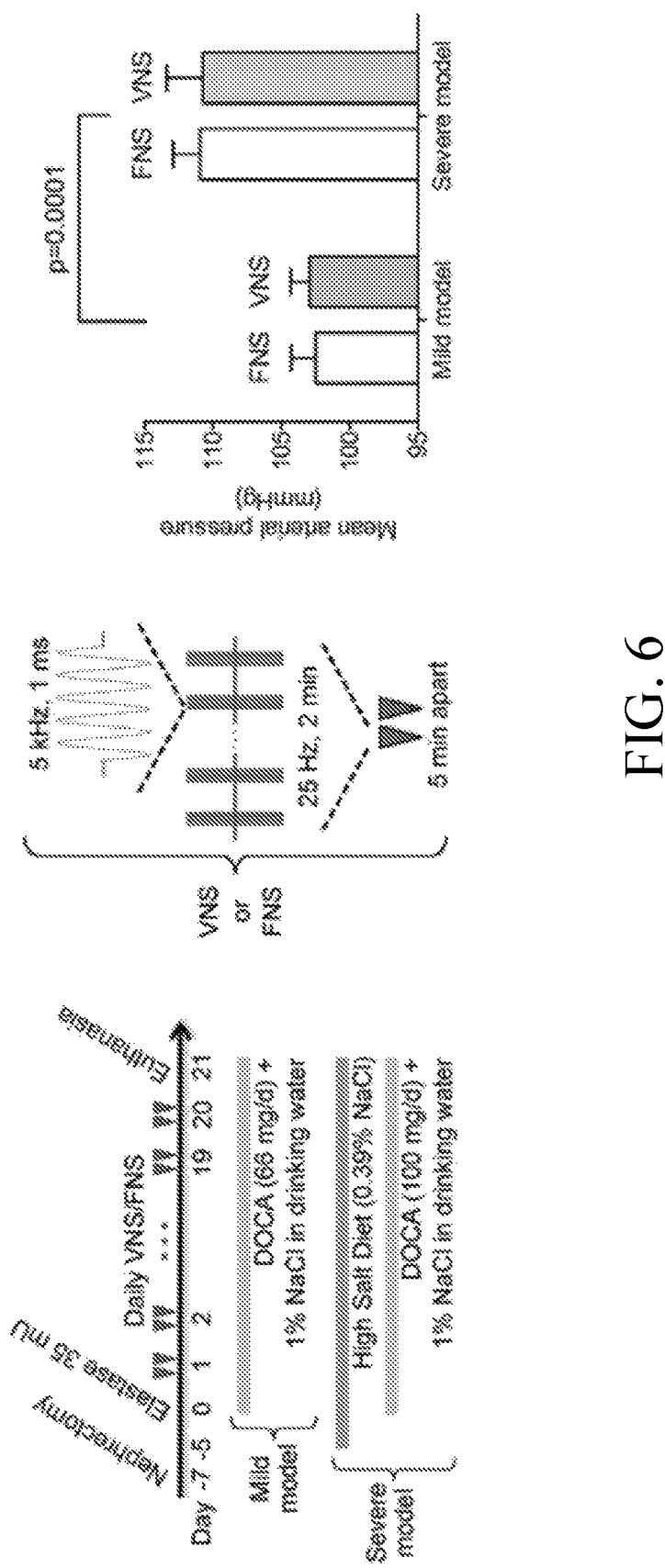
FIG. 6 is a timeline, an illustration, and a graph for the experimental protocol, as detailed in one, non-limiting example in accordance with the present disclosure.

FIG. 6 shows experimental protocols in the form of a timeline, an illustration, and graphs. The upper left experimental timeline shows the timing and procedures to develop the aneurysm induction model. For example, the mild and severe model differences in deoxycorticosterone acetate ("DOCA") dosing, and the high-salt diet. The central illustration shows the transcutaneous electrical stimulus to achieve VNS or FNS, which consisted of 1 millisecond, 5 kHz sine wave pulses, delivered at 25 Hz (e.g., 25 times) over 2 min. This was repeated once, five minutes apart. The graphs on the right show that the severe model consistently yielded higher arterial blood pressures than the mild model ($P<0.001$) without a difference between VNS and FNS groups (2-way ANOVA).

Figure 7:
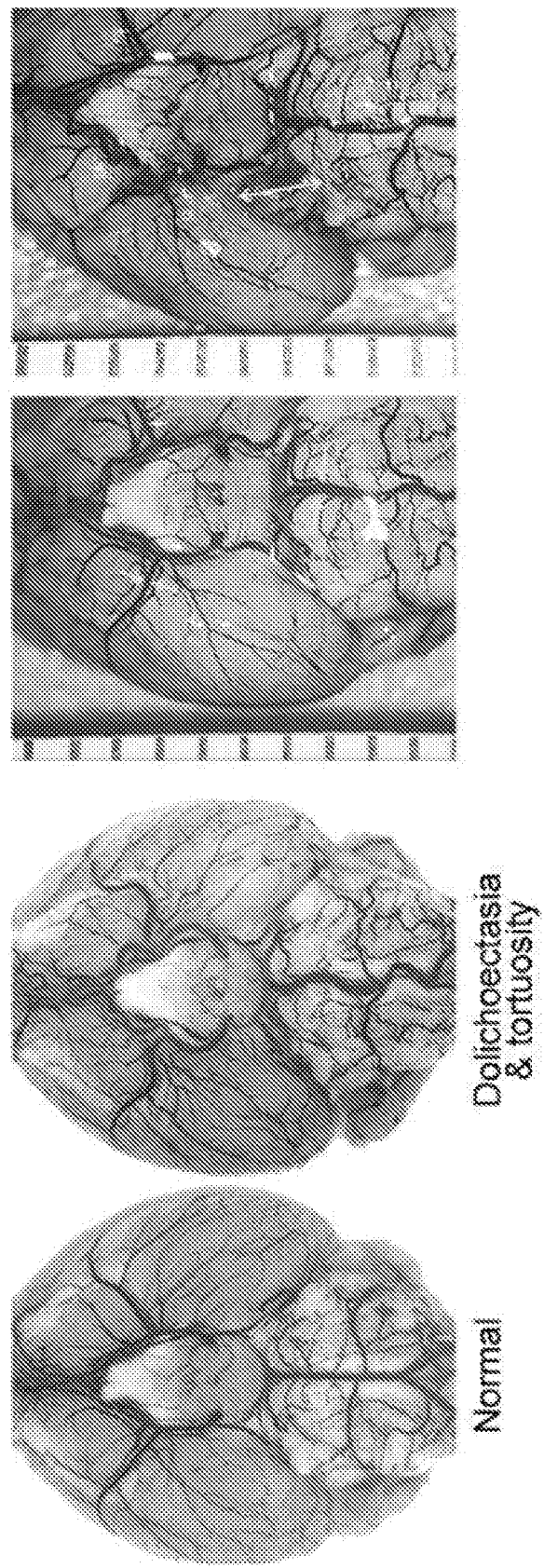
FIG. 7 is a series of images of mouse brains from the non-limiting example.

FIG. 7 shows images of the brains from the study. When comparing the normal brain to the dolichoectasia and tortuosity brain, gross morphological changes in the large cerebral arteries becomes apparent. The two images on the left side of FIG. 7 show the method to determine the presence or absence of tortuosity. More specifically, the two images on the right side show the process of aneurysmal diameter measurements as readouts using an on-field millimeter scale. The largest visible diameter of each aneurysm was measured.

Figure 8:
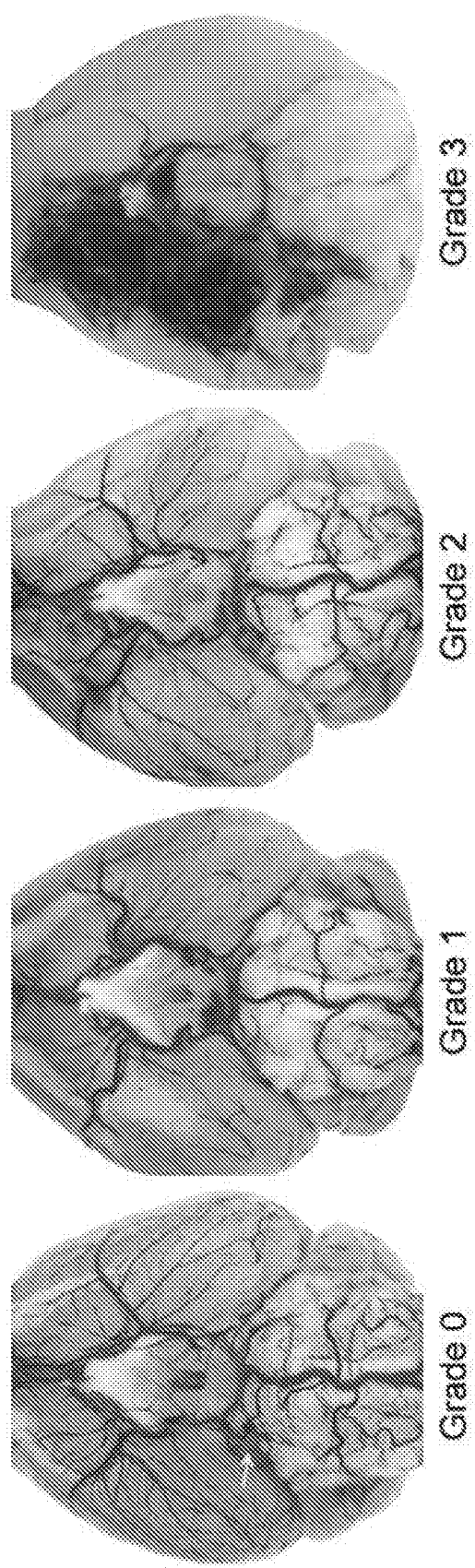
FIG. 8 is another series of images of mouse brains detailing the various grades of subarachnoid hemorrhage in accordance with the present disclosure.

FIG. 8 also show images of the brains from the study. The represented brains show typical examples for subarachnoid hemorrhage (SAH) grades 0 to 3, which was used to quantify SAH severity.

FIG. 9 shows four charts each showing results of the primary outcomes. More specifically, the upper row of charts show survival percentage curves, while the lower row of charts show the deficit-free survival curves, both for femoral nerve stimulation ("FNS") and vagus nerve stimulation ("VNS"), and for each of the models (e.g., mild (left) and severe (right)). The breakdown for the models had n=10 FNS and 14 VNS in the mild model, and 13 each in the severe model (and utilized a Gehan-Breslow-Wilcoxon test).

Figure 10:
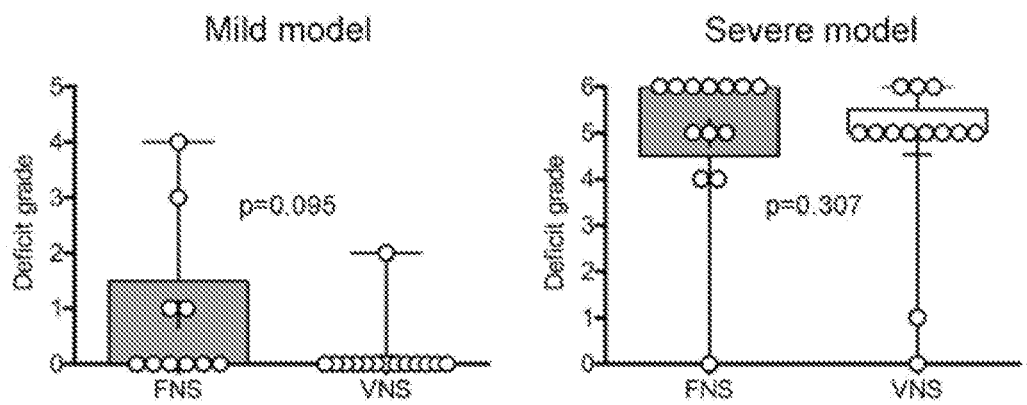
FIG. 10 is another series of graphs showing the deficit grade for both models, and between both groups.

FIG. 10 shows two charts having neurological deficit grades for mild (left) and severe (right) models. Each data point reflects 1 animal (Mann-Whitney test).

Figure 11:
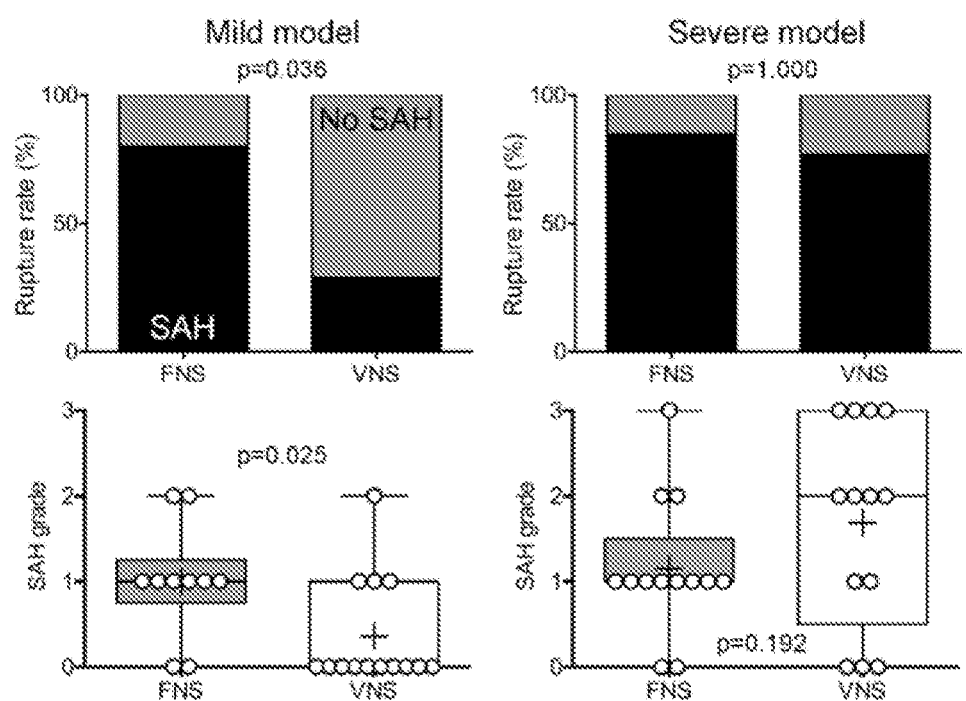
FIG. 11 is another series of graphs showing the aneurysm rupture percentage, and subarachnoid hemorrhage grade for both models, and between both groups.

FIG. 11 shows SAH grades (lower row) for mild (left) and severe (right) models. FIG. 11 also shows rupture compared between FNS and VNS. The Fisher exact test was used for rupture rates, while the Mann-Whitney test was used for subarachnoid hemorrhage (SAH) grades.

Figure 12:
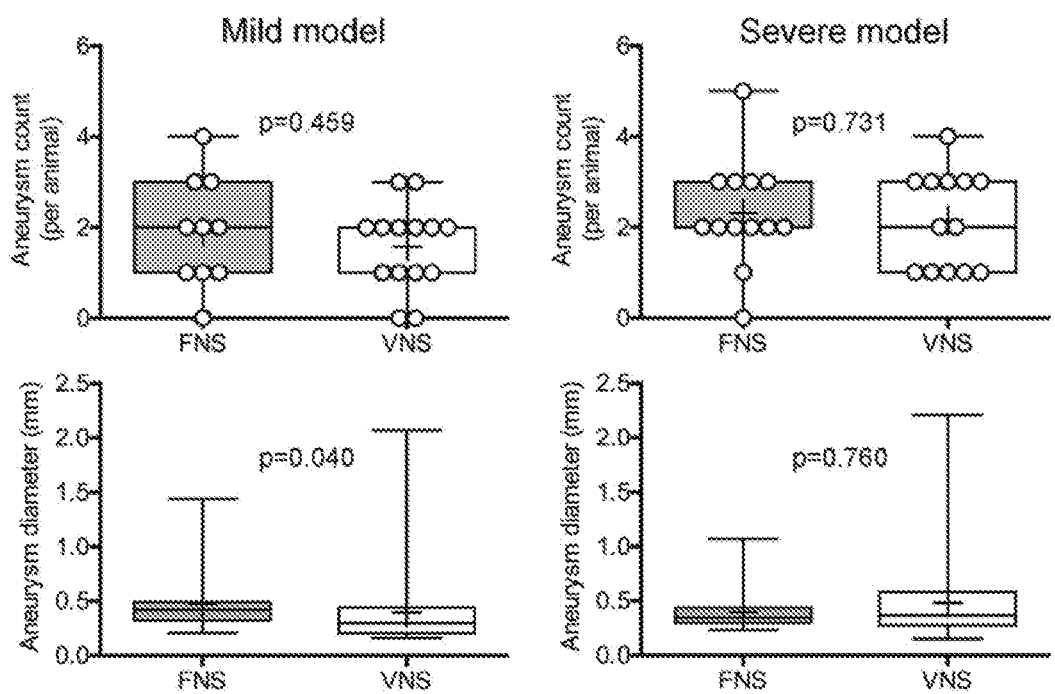
FIG. 12 is another series of graphs showing the aneurysm count, and aneurysm diameter for both models, and between both groups.

FIG. 12 shows four graphs indicating the aneurysm count and the aneurysm diameter. The upper row shows aneurysm count per animal, while the lower row shows aneurysm diameters, each for the mild (left) and the severe (right) models. The numbers of mice were as follows: 10 femoral nerve stimulation ("FNS"), 14 vagus nerve stimulation ("VNS") in the mild model, and 13 each in the severe model. The aneurysm counts were compared between the FNS group and the VNS group using an unpaired t test. The aneurysm diameters were as follows: n=19 FNS, 22 VNS in the mild model, 30 FNS, and 28 VNS in the severe model. The aneurysm diameters were compared between FNS and VNS using a Mann-Whitney test for non-normally distributed data.

FIG. 13 shows illustrated aneurysm distribution map of a brain for each model. More specifically, FIG. 13 shows the aneurysm size and distribution maps for mild (left) and severe (right) models for FNS (black) and VNS (grey). The crosses (and corresponding arrows) indicate the injection site.

FIG. 14 shows graphs of the aneurysm distance between the two models. More specifically, the aneurysm distance to the injection site for mild (left) and severe (right) models are shown (e.g., the number of aneurysms as in FIG. 13, and using an unpaired t test with Welch correction for unequal variances).

Figure 15:
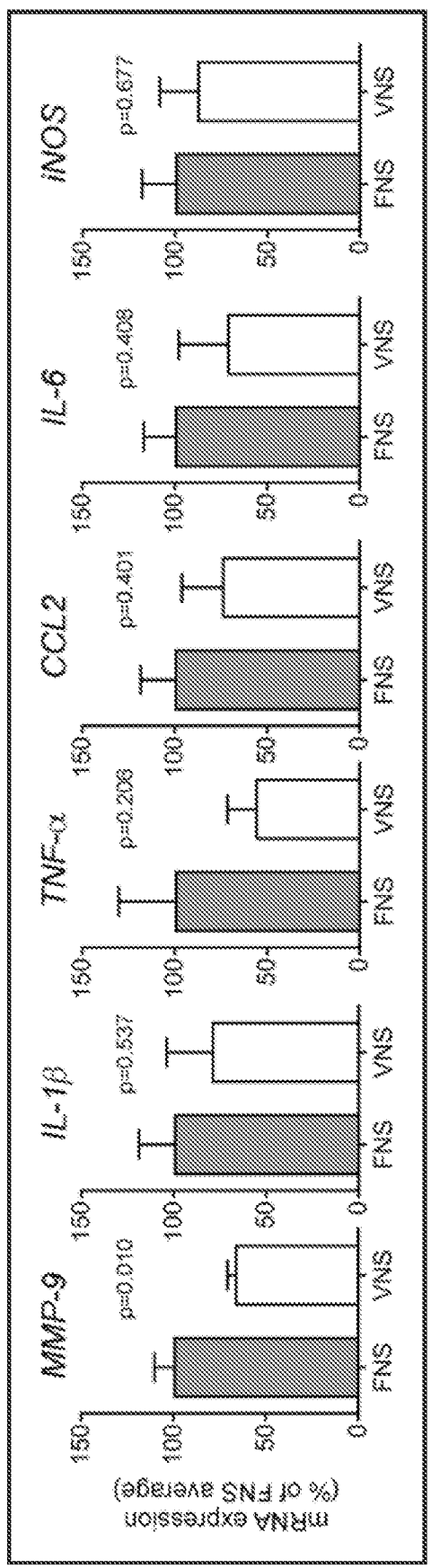
FIG. 15 is another series of graphs showing the messenger RNA ("mRNA") expression for various genes, compared between both groups.

FIG. 15 shows graphs indicating the proinflammatory gene expression within the circle of Willis for each type of stimulation (e.g., VNS vs. FNS). FIG. 15 shows exploratory data on the mRNA expression of proinflammatory genes within the circle of Willis in femoral nerve stimulation (FNS)- or vagus nerve stimulation (VNS)-treated mice, 4 days after elastase injection (n=5 FNS, 6 VNS; unpaired t test). CCL2 indicates chemokine C-C motif ligand 2; IL-1β, interleukin-1β; IL-6, interleukin-6; iNOS, inducible nitric oxide synthase; and MMP-9, matrix metalloproteinase-9.

Figure 16:
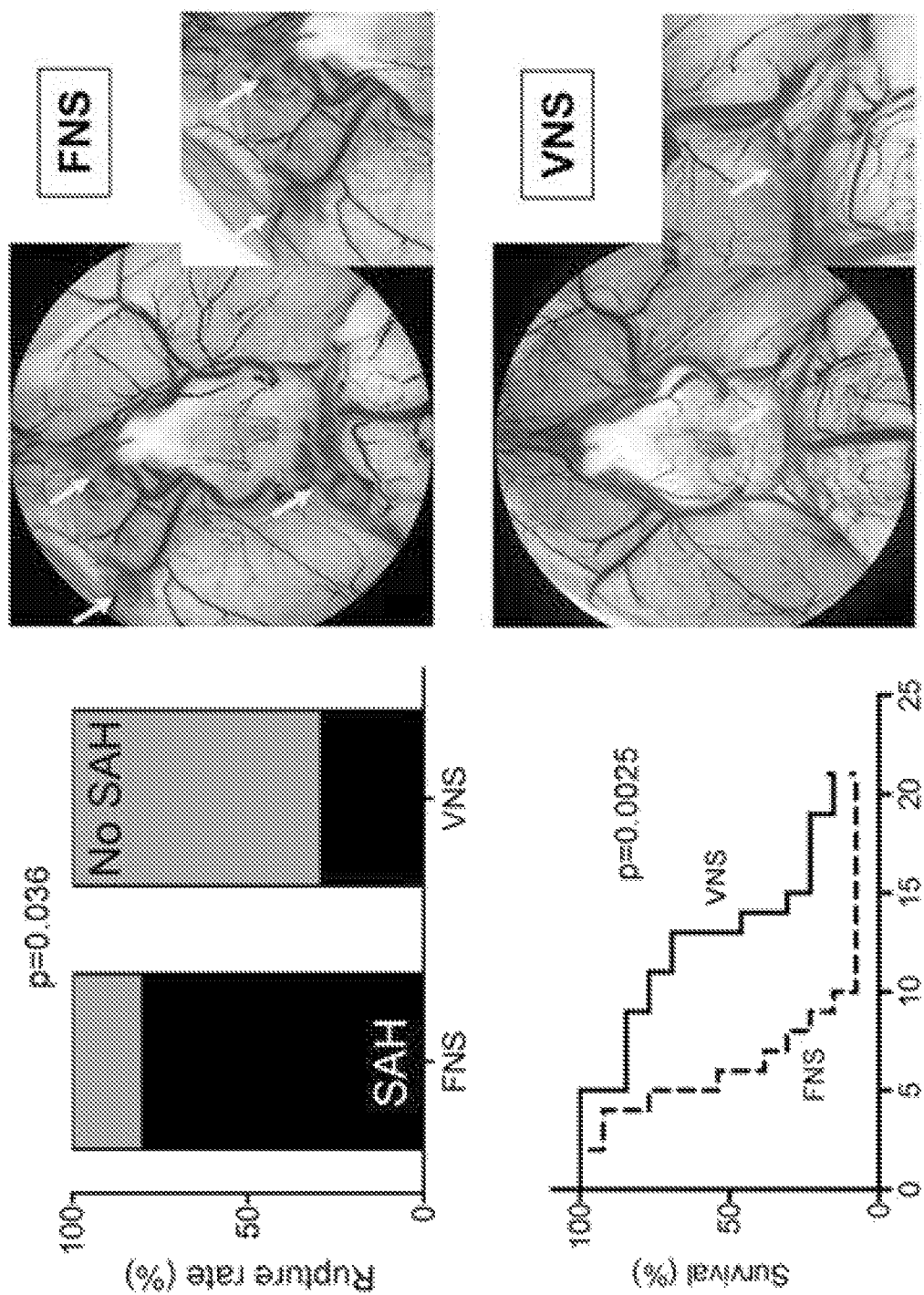
FIG. 16 is a series of graphs, and images of mouse brains from the non-limiting example.

FIG. 16 shows graphs and images of mouse brains, which summarize the non-limiting example. Overall, in the non-limiting example, an experimental intracranial aneurysm mouse model with two levels of severity was used, to test the effect of a novel non-invasive transcutaneous vagus nerve stimulation (VNS). In the mild model, VNS significantly reduced aneurysm rupture rate compared with femoral nerve stimulation (FNS) (29% vs. 80%, respectively). In the severe model, it improved the survival rate compared with FNS after aneurysm rupture (median survival 13 vs. 6 days, respectively). Chronic daily VNS reduced matrix metalloprotease-9 expression compared with FNS, providing a potential mechanism for the prevention of intracranial aneurysm rupture.

TABLE 1

Vessel diameters (2-way ANOVA for repeated measures) and presence of tortuosity (Fisher exact test) did not differ between FNS and VNS groups.

| | Mild Model | | | Severe Model | | |
|---|---|---|---|---|---|---|
| | FNS (n = 14) | VNS (n = 14) | P Value | FNS (n = 13) | VNS (n = 13) | P Value |
| | Tortuosity (% present) | | | | | |
| Ipsilateral anterior circulation | 70% | 79% | 0.665 | 69% | 77% | 1.00 |
| Contralateral anterior circulation | 60% | 21% | 0.092 | 77% | 77% | 1.00 |
| Basilar artery | 90% | 100% | 0.417 | 100% | 100% | 1.00 |
| Diameters, μm | | | 0.462 | | | |
| Ipsilateral ICA | 189 ± 13 | 212 ± 13 | | 166 ± 14 | 174 ± 12 | |
| Contralateral ICA | 184 ± 18 | 154 ± 10 | | 167 ± 8 | 170 ± 10 | |
| Ipsilateral ACA | 162 ± 11 | 159 ± 13 | | 141 ± 10 | 159 ± 11 | |
| Contralateral ACA | 151 ± 16 | 132 ± 8 | | 142 ± 7 | 148 ± 8 | |

TABLE 1-continued

Vessel diameters (2-way ANOVA for repeated measures) and presence of tortuosity (Fisher exact test) did not differ between FNS and VNS groups.

| | Mild Model | | | Severe Model | | |
|---|---|---|---|---|---|---|
| | FNS (n = 14) | VNS (n = 14) | P Value | FNS (n = 13) | VNS (n = 13) | P Value |
| | | Tortuosity (% present) | | | | |
| Ipsilateral MCA | 169 ± 11 | 160 ± 9 | | 134 ± 9 | 158 ± 9 | |
| Contralateral MCA | 157 ± 15 | 136 ± 6 | | 131 ± 5 | 142 ± 7 | |
| Basilar artery | 221 ± 19 | 217 ± 8 | | 197 ± 14 | 211 ± 10 | |

ACA indicates anterior cerebral artery;
FNS, femoral nerve stimulation;
ICA, internal carotid artery;
MCA, middle cerebral artery; and
VNS, vagus nerve stimulation.

Thus, we tested the effect of a novel noninvasive transcutaneous VNS approach on aneurysm rupture and outcome in a mouse model of intracranial aneurysm formation with wall inflammation. In the study, aneurysms were induced by a single stereotaxic injection of elastase into the cerebrospinal fluid at the skull base, combined with systemic deoxycorticosterone-salt hypertension, without or with high-salt diet, for mild or severe outcomes, respectively. Cervical VNS (two 2-minute stimulations 5 minutes apart) was delivered once a day starting from the day after elastase injection for the duration of follow up. Transcutaneous stimulation of the femoral nerve (FNS) served as control. Multiple aneurysms developed in the circle of Willis and its major branches, resulting in spontaneous ruptures and subarachnoid hemorrhage, neurological deficits, and mortality. The results of the milder model show that VNS significantly reduced aneurysm rupture rate compared with FNS (29% versus 80%, respectively). Subarachnoid hemorrhage grades were also lower in the INS group. Conversely, in the more severe model, both VNS and FNS arms developed very high rupture rates (77% and 85%, respectively). However, and importantly, VNS significantly improved the survival rate compared with FNS after rupture (median survival 13 versus 6 days, respectively), without diminishing the subarachnoid hemorrhage grades. Chronic daily VNS reduced matrix metalloproteinase-9 expression compared with FNS, providing a potential mechanism of action (without being bound by theory). As an important control, chronic daily VNS did not alter systemic arterial blood pressure compared with FNS.

It should be understood that the above described steps of the process of FIG. 5 can be executed or performed in any order or sequence not limited to the order and sequence shown and described in the figures. Also, some of the above steps of the process of FIG. 5 can be executed or performed substantially simultaneously where appropriate.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

The invention claimed is:

1. A method for improving a patient outcome for a subject having an aneurysm, the method comprising:
   determining that the subject has the aneurysm;
   based on the determination of the aneurysm, selecting or adjusting parameters of an electrical stimulation to be provided to the vagus nerve of the subject;
   positioning a vagus nerve stimulation system on the subject, the vagus nerve stimulation system being configured to provide the electrical stimulation to the vagus nerve of the subject;
   stimulating the vagus nerve of the subject with the vagus nerve stimulation system to at least one of:
   prevent further growth of the aneurysm;
   decrease a likelihood that the aneurysm ruptures; or
   decrease effects of rupture, when the aneurysm of the subject ruptures.

2. The method of claim 1, wherein the stimulation of the vagus nerve decreases at least one of a level of matrix metalloproteinase-9 (MMP-9) in the subject or a gene expression of MMP-9 in the subject.

3. The method of claim 1, further comprising:
   acquiring an image of a head of the subject using an imaging system; and
   determining that the subject has the aneurysm by analyzing the image of the head of the subject to locate the aneurysm.

4. The method of claim 1, wherein stimulating includes delivering an electrical waveform having a frequency and wherein the frequency is in a range between 1 Hz and 10 kilohertz (kHz), and
   wherein a portion of the electrical waveform is negative, and a portion of the electrical waveform is positive.

5. The method of claim 4, wherein the electrical waveform has a pulse width between 0.1 milliseconds and 1 second.

6. The method of claim 1, wherein the vagus nerve stimulation system includes a signal generator, a first magnetic coil, a second magnetic coil, a first electrically conducive medium disposed within the first magnetic coil, and a second electrically conductive medium disposed within the second magnetic coil, the signal generator being in communication with the first magnetic coil and the second magnetic coil,
   wherein stimulating the vagus nerve of the subject with the vagus nerve stimulation system includes:
   causing the signal generator to emit an electrical waveform to the first magnetic coil and the second magnetic coil, the electrical waveform having a frequency.

7. The method of claim 1, wherein stimulating the vagus nerve of the subject with the vagus nerve stimulation system includes:
  stimulating the vagus nerve of the subject for a first duration; and
  stimulating the vagus nerve of the subject for a second duration.

8. The method of claim 7, further comprising waiting a third duration after the first duration.

9. The method of claim 8, wherein the third duration spans a time period, such that the first duration spans at least a portion of a first day and the second duration spans at least a portion of a second day.

10. The method of claim 8, wherein the first duration and the second duration is two minutes, and wherein the third duration is five minutes.

11. The method of claim 1, wherein the vagus nerve stimulation system is configured to non-invasively stimulate the vagus nerve of the subject.

12. The method of claim 1, wherein decreased effects of rupture include at least one of increased likelihood of survival, decreased neurological deficits, or improved quality of life.

13. A method for improving a patient outcome for a subject having an aneurysm, the method comprising:
  determining that the subject has the aneurysm;
  positioning a vagus nerve stimulation system on the subject, the vagus nerve stimulation system being configured to provide an electrical stimulation to the vagus nerve of the subject;
  stimulating the vagus nerve of the subject with the vagus nerve stimulation system to at least one of:
    prevent further growth of the aneurysm;
    decrease a likelihood that the aneurysm ruptures; or
    decrease effects of rupture, when the aneurysm of the subject ruptures;
  wherein the stimulation of the vagus nerve decreases at least one of a level of matrix metalloproteinase-9 (MMP-9) in the subject or a gene expression of MMP-9 in the subject;
  wherein the stimulation of the vagus nerve decreases the gene expression of MMP-9 in the subject by:
    decreasing an amount of mRNA in the subject corresponding to MMP-9; and
    decreasing an amount of MMP-9 in the subject by the decreased translation from the decreased amount of mRNA in the subject corresponding to MMP-9.

14. A method for improving a patient outcome for a subject having an aneurysm, the method comprising:
  determining that the subject has the aneurysm;
  positioning a vagus nerve stimulation system on the subject, the vagus nerve stimulation system being configured to provide an electrical stimulation to the vagus nerve of the subject;
  stimulating the vagus nerve of the subject with the vagus nerve stimulation system to at least one of:
    prevent further growth of the aneurysm;
    decrease a likelihood that the aneurysm ruptures; or
    decrease effects of rupture, when the aneurysm of the subject ruptures;
  further comprising repeating stimulating the vagus nerve of the subject with the vagus nerve stimulation system daily for at least one of: a week, a month, or two months.

* * * * *